US009993541B2

(12) United States Patent
Winther-Larsen et al.

(10) Patent No.: US 9,993,541 B2
(45) Date of Patent: Jun. 12, 2018

(54) OUTER MEMBRANE VESICLES AND USES THEREOF

(71) Applicants: UNIVERSITY OF OSLO, Oslo (NO); NMBU VETERINæRHØGSKOLEN, Åa (NO); VETERINæRINSTITUTTET, Oslo (NO)

(72) Inventors: Hanne Winther-Larsen, Oslo (NO); Espen Brudal, Oslo (NO); Duncan Colquhoun, Hakadal (NO)

(73) Assignees: UNIVERSITY OF OSLO, Oslo (NO); NIMBU VETERINÆRHØGSKOLEN, Ås (NO); VETERINÆRINSTITUTTET, Sentrum (NO)

( * ) Notice: Subject to any disclaimer, the term of this patent is extended or adjusted under 35 U.S.C. 154(b) by 0 days. days.

(21) Appl. No.: 15/034,330

(22) PCT Filed: Nov. 13, 2014

(86) PCT No.: PCT/IB2014/003033
§ 371 (c)(1),
(2) Date: May 4, 2016

(87) PCT Pub. No.: WO2015/071769
PCT Pub. Date: May 21, 2015

(65) Prior Publication Data

US 2016/0279222 A1 Sep. 29, 2016

Related U.S. Application Data

(60) Provisional application No. 61/903,684, filed on Nov. 13, 2013.

(51) Int. Cl.

| | |
|---|---|
| *A01N 63/00* | (2006.01) |
| *A61K 39/02* | (2006.01) |
| *A61K 39/00* | (2006.01) |

(52) U.S. Cl.
CPC ...... *A61K 39/0233* (2013.01); *A61K 39/0208* (2013.01); *A61K 2039/552* (2013.01)

(58) Field of Classification Search
CPC .................................................. A61K 39/0233
See application file for complete search history.

(56) References Cited

FOREIGN PATENT DOCUMENTS

| | | | |
|---|---|---|---|
| WO | 1997/05899 | 2/1997 | |
| WO | WO-2005035558 A2 * | 4/2005 | ........... C07K 14/195 |
| WO | 2007/047501 | 4/2007 | |
| WO | 2012/097185 | 7/2012 | |
| WO | 2015/074943 | 5/2015 | |
| WO | 2015/074946 | 5/2015 | |

OTHER PUBLICATIONS

Alaniz, R. C., B. L. Deatherage, J. C. Lara, and B. T. Cookson. 2007. Membrane vesicles are immunogenic facsimiles of *Salmonella typhimurium* that potently activate dendritic cells, prime B and T cell responses, and stimulate protective immunity in vivo. J.Immunol. 179:7692-7701.

Bakkemo et al., "Intracellular localization and innate immune responses following Francisella noatunensis infection of Atlantic cod (*Gadus morhua*) macrophages." Fish & Shellfish Immunology 31(6) (2011) pp. 993-1004.

Cole et al. "Antigen-specific B-1a antibodies induced by Francisella tularensis LPS provide long-term protection against F. tularensis LVS challenge." 2009, Proc.Natl.Acad.Sci.U.S.A 106(11):4343-4348.

Collins, B. S. "Gram-negative outer membrane vesicles in vaccine development." Discov. Med., 2011, 12:7-15.

Colquhoun, D. J. and S. Duodu. 2011. "Francisella infections in farmed and wild aquatic organisms." Vet.Res. 42:47.

Conlan, J. W. and P. C. Oyston. 2007. Vaccines against Francisella tularensis. Ann.N.Y.Acad.Sci. 1105:325-50.

International Search Report, International Patent Application No. PCT/IB2014/003033, dated Jun. 9, 2015.

McCaig, W. D., A. Koller, and D. G. Thanassi. 2013. Production of outer membrane vesicles and outer membrane tubes by Francisella novicida. J.Bacteriol. 195:1120-1132.

Nieves, W., S. Asakrah, O. Qazi, K. A. Brown, J. Kurtz, D. P. Aucoin, J. B. McLachlan, C. J. Roy, and L. A. Morici. 2011. A naturally derived outer-membrane vesicle vaccine protects against lethal pulmonary Burkholderia pseudomallei infection. Vaccine 29(46):8381-8389.

Park et al. "Outer Membrane Vesicles as a Candidate Vaccine against Edwardsiellosis" PLOS One, vol. 6, No. 3, Jan. 1, 2011, p. e17629.

Pierson et al., "Proteomic characterization and functional analysis of outer membrane vesicles of Francisella novicida suggests possible role in virulence and use as a vaccine." J Proteome Res. Mar. 4, 2011;10(3):954-67.

Schild, S., E. J. Nelson, and A. Camilli. 2008. "Immunization with Vibrio cholerae outer membrane vesicles induces protective immunity in mice." Infect.Immun. 76(10):4554-4563.

Sebastian, S., et al.. 2007. A defined O-antigen polysaccharide mutant of Francisella tularensis live vaccine strain has attenuated virulence while retaining its protective capacity. Infect.Immun. 75:2591-2602.

Soto, E. et al. "Attenuated Francisella asiatica igIC mutant induces protective immunity to francisellosis in tilapia." Vaccine. Jan. 10, 2011;29(3):593-8.

Aoki et al. "Stationary phase culture supernatant containing membrane vesicles induced immunity to rainbow trout Oncorhynchus mykiss fry syndrome" VAC, vol. 25, No. 3, Dec. 8, 2016, pp. 561-569.

(Continued)

*Primary Examiner* — Albert M Navarro
(74) *Attorney, Agent, or Firm* — Casimir Jones S.C.; J. Mitchell Jones

(57) ABSTRACT

The disclosure relates to outer membrane vesicles from *Francisella* and *Piscirickettsia*, and their use in vaccine compositions. In particular, the present disclosure relates to compositions and methods useful in inducing protective immunity against francisellosis or salmon rickettsial septicaemia (SRS) in fish.

4 Claims, 12 Drawing Sheets

(56) References Cited

OTHER PUBLICATIONS

Rojas et al. "Evidence of exotoxin secretion of Piscirickettsia salmonis, the causative agent of piscirickettsiosis" Journal of Fish Diseases, vol. 36, No. 8, Aug. 2013, pp. 703-709.
Gomez, F. et al. "Evidence of the Presence of a Funtional Dot/Icm Type IV-B Secretion System in the Fish Bacterial Pathogen Piscirickettsia salmonis" PLOS One, vol. 8, No. 1, 2013, p. e54934.
Kuzyk, M. A. et al. "Ospa, a Lipoprotein Antigen of the Obligate Intracellular Bacterialpathogen Piscirickettsia salmonis" Journal of Molecular Microbiology and Biotechnology, vol. 3, No. 1, Jan. 2001, pp. 83-93.
EP Search Report, EP Patent Application No. 14835493.9, dated Dec. 5, 2017, 4 pages.

\* cited by examiner

A.

B.

C.

D.

OUTER MEMBRANE VESICLES AND USES THEREOF

FIELD OF THE INVENTION

The disclosure relates to outer membrane vesicles from microorganisms, and their use in vaccine compositions. In particular the disclosure relates to outer membrane vesicles from *Francisella* and *Piscirickettsia*, and their use in vaccine compositions. The disclosure relates to outer membrane vesicles from *Francisella* and *Piscirickettsia*, and their use in vaccine compositions. In particular, the present disclosure relates to compositions and methods useful in inducing protective immunity against francisellosis or salmon rickettsial septicaemia (SRS) in fish.

BACKGROUND OF THE INVENTION

*Francisella* species (spp) are non-motile, pleomorphic, gram-negative, strictly aerobic, facultative intracellular coccobacilli. They are extremely infectious, as less than 10 bacteria are required for infection (Jones et al., 2005; Soto et al., 2009; Kamaishi et al., 2010). One member of the genus, *Francisella noatunensis*, has been reported worldwide as a cause of francisellosis in fish (Kamaishi et al., 2005; Mauel et al., 2005; Olsen et al., 2006; Mauel et al., 2007; Birkbeck et al., 2007; Jefferery et al., 2010). *F. noatunensis* is composed of two subspecies adapted to different host temperatures, one of which (*F. noatunensis* ssp. *orientalis*) causes disease in fish living in warmer waters (Kamaishi et al., 2005; Mauel et al., 2005; Mauel et al., 2007; Jeffery et al., 2010) while the second (*F. noatunensis* ssp. *noatunensis*) causes disease in fish living in colder waters (Nylund et al., 2006; Olsen et al., 2006; Birkbeck et al., 2007). Outbreaks of francisellosis in fish aquaculture can be devastating, causing large losses worldwide (Kamaishi et al., 2005; Mauel et al., 2005; Olsen et al., 2006; Mauel et al., 2007; Birkbeck et al., 2007; Jefferery et al., 2010), and represents the main challenge for aquaculture based on Atlantic cod *Gadus morhua* L. It is also sporadically problematic in aquaculture base on Tilapia, one of the largest produced fish worldwide.

*Piscirickettsia salmonis* is described as non-motile, not-encapsulated, pleomorphic coccoid, with a size ranging from 0.1-1.5 um (Mauel and Miller, 2002, Vet Microbiol, 87:279-289). Salmon Rickettsial Septicaemia (SRS), caused by *P. salmonis*, is a disease of salmonid fish with a huge impact on the salmonid fish farming particularly in Chile. Similarly to *Francisella* sp., also *P. salmonis* is intracellular in nature making vaccine development challenging. The mortality rate of affected fish varies, from more than 90% mortality in some Chilean outbreaks, to low levels of mortality in e.g. Norway. The reason for the observed differences in mortality is not known, and although environmental factors must be taken into account, strain difference is also likely. As annual losses due to SRS in Chile are estimated to be more than 200 million USD each year, the potential impact on the salmon aquaculture could be devastating. Despite the availability of several commercial vaccines against SRS with reported good efficacy in laboratory trials (Wilhelm et al., 2006, Vaccine, 24:5083-5091; list of available vaccines are reviewed in the Australian Aquatic Veterinary Emergency Plan, Disease Strategy Piscirickettsiosis, 2013), SRS was reported as responsible for 60% of the mortality of salmon and 79% of the mortality rainbow trout in Chile in 2011 (Integrated Annual and Sustainability Report 2012, Cermaq: EWOS Innovation-SRS project in Chile). Clearly, there is a demand for a vaccine against SRS with improved efficacy. Up until recently, one of the main challenges within *P. salmonis* research and vaccine development has been the lack of growth of the pathogen in liquid culture media. Yañez et al., (2012), reported the AUSTRAL-SRS broth, a highly complex medium consisting of a marine-based broth supplemented with L-cysteine, that supported the growth of *P. salmonis* reaching an optical density of approx $OD_{600\ nm}=1.8$ after 6 days incubation. Improvements of growth rate and increased biomass was made by growth in basal medium 3 (BM3) reaching an $OD_{600\ nm}$ of 1.7 after 37.5 hrs (Henriquez et al., 2013). BM3 consist of yeast extract (Merck) 2.0 g L21, peptone from meat (peptic digested, Merck) 2.0 g/L, $MgSO_4*7H_2O$ 0.1 g/L, $K_2HPO_4$ 6.3 g/L, NaCl 9.0 g/L, $CaCl_2*2H_2O$ 0.08 g/L, $FeSO_4*7H_2O$ 0.02 g/L and glutamic acid 2 g/L.

Aquaculture is able to prevent outbreaks of many bacterial infections that presented huge problems for the industry in its youth, by the use of vaccines composed of inactivated in vitro cultured whole-cell bacterial preparations (bacterins) supplemented with adjuvants (reviewed by Brudeseth et al., 2013). As a consequence of this, the use of antimicrobials in Norwegian aquaculture has declined enormously despite a large increase in the amount of fish produced (reviewed by Sommerset et al., 2005). No commercial vaccine for fish francisellosis is currently available (reviewed by Colquhoun & Duodu, 2011; reviewed by Brudeseth et al., 2013), as attempts at using whole-cell preparations of *F. noatunensis* ssp. *noatunensis* has yielded none or unsatisfactory levels of protection (reviewed by Colquhoun & Duodu, 2011). This is similar to the situation for tularemia in humans, where vaccination with killed bacteria induces an antibody response with only limited protective properties (reviewed by Cowley and Elkins, 2011). The reason for this is due to the fact that to develop proper protection against *Francisella* spp. there is a need to stimulate cell-mediated immunity (reviewed by Cowley and Elkins, 2011), which vaccines based on killed whole-cells or protein subunits generally are poor at (reviewed by Titball, 2008). Live attenuated vaccines (LAVs) are efficient at inducing cell-mediated immunity, though there are safety concerns such as reversion to virulence and safety for immune-compromised individuals for such vaccines (reviewed by Titball, 2008). Particularly in an aquaculture setting, spread of genetically modified organisms to the environment is another factor to take into account. A LAV designated Live Vaccine Strain (LVS) has successfully been utilized to protect high-risk groups against tularemia (reviewed by Conlan & Oyston, 2007), demonstrating that it is possible to generate successful LAVs against *Francisella* spp. Several targeted deletion strains have also been shown to be protective against tularemia, such as the *F. tularensis* ssp. *tularensis* Schu S4 Δftt_0918, Δftt_0918ΔcapB and ΔclpB (reviewed by Conlan & Oyston, 2007, Conlan et al., 2010). Additionally, a LAV based on a ΔiglC mutant of *F. noatunensis* ssp. *orientalis* has recently been patented (U.S. Pat. No. 8,147,820 B2) for use against francisellosis in aquaculture, and has been shown to protect tilapia against experimental challenge (Soto et al., 2011). Previous ΔiglC mutants have been shown to induce protective immunity in mice for *F. tularensis* ssp. *novicida* but not against *F. tularensis* ssp. *tularensis* (Twine et al., 2005; Pammit et al., 2006). Protection obtained by vaccination with both *F. tularensis* ssp. *novicida* and *F. noatunensis* ssp. *orientalis* ΔiglC mutants in mice and tilapia respectively could partly be transferred by passive immunization of naïve animals (Pammit et al., 2006; Soto et al., 2011).

When constructing vaccines for immunization of Atlantic cod there are certain peculiarities of the cod immune system that should be addressed. Vaccination results in production of lower levels of specific antibodies and less variety in the utilization of immunoglobulin heavy chain types, but despite this Atlantic cod develop protective immunity after vaccination with most bacterial pathogens (reviewed by Samuelsen et al., 2006). The reason for this was for a long time unclear, however difficulties with identifying MHC class II and associated genes indicated changes in how Atlantic cod process classical MHC class II dependent antigens. Recently whole-genome sequencing revealed that the genome of Atlantic cod lack MHC class II and Invariant chain (Ii), and that CD4 is only present as a truncated pseudogene (Star et al., 2011). This would render the MHC class II antigen presenting pathway (Mantegazza et al., 2013) non-functional, and would explain the lack of specific antigen-responses when vaccinating with bacterins. Atlantic cod has expanded its repertoire of MHC class I antigens which might facilitate cross-presentation of traditional MHC class II antigens by MHC class I molecules, and there is evidence that Atlantic cod might be compensating for the loss of CD4$^+$ T-cells as well by having different subsets of CD8$^+$ T-cells (Star et al., 2011). Atlantic cod also has high levels of natural antibodies compared to other fish species (reviewed by Pilström et al., 2005), which might compensate for a strong specific antibody response on encounter with a pathogen. However, there are reports of Atlantic cod producing specific antibodies in response to vaccination with *Aeromonas salmonicida, Listonella (Vibrio) anguillarum* and *F. noatunensis* (Lund et al., 2006; Lund et al., 2007; Schrøder et al., 2009), though as they seem to be predominately recognizing LPS a T-cell independent antibody response (reviewed by Alugupalli, 2008) could explain the observed production of antibodies in response to these bacterial pathogens.

The production of membrane vesicles by cells is a conserved mechanism occurring throughout all domains of life, both prokaryotic and eukaryotic (reviewed by Deatherage & Cookson, 2012). In bacteria, these vesicles are usually called Outer Membrane Vesicles (OMVs) and are formed by budding from the outer bacterial membrane (from Gram negative bacteria). They are 10-300 nm in diameter and spherical, containing outer membrane and periplasmic proteins, and recent data indicates that they might contain inner membrane and cytoplasmic proteins as well, and in some cases DNA (Pèrez-Cruz et al., 2013+++). The protein content of OMVs show specific packaging, as some proteins are enriched and some are excluded (e.g. Galka et al., 2011; Haurat et al., 2011 og mange flere). The exact sorting mechanism responsible for enrichment or exclusion of proteins from OMVs is not currently known. Many pathogenic bacteria incorporate virulence factors, including toxins, into their OMVs, turning the vesicles into bacterial-derived bombs (Kuehn & Kesty, 2005; Galka et al., 2011; Haurat et al., and etec+salmonella as well). OMVs have recently received renewed focus in the field of vaccinology (reviewed by Collins, 2011), as they present antigens in their native conformation and does not require adjuvants to be immunogenic. Immunization of humans using OMVs have been performed with great success against *Neisseria meningitidis* type B (reviewed by Granoff, 2010; Collins, 2011). OMVs derived from other bacteria have also shown protective efficacy when used as vaccines against other pathogenic bacteria, such as *Burkholderia pseudomallei* (Nieves et al., 2011), *Brucella melitensis* (Avila-Calderòn et al., 2012), *Edwardsiella tarda* (Park et al., 2011), enterotoxigenic *Escherichia coli* (Roy et al., 2011), *Salmonella* Typhimurium (Alaniz et al., 2007), *Shigella flexneri* (Camacho et al., 2011; Camacho et al., 2013) and *Vibrio cholera* (Schild et al., 2008). OMVs have been shown to induce both B- and T-cell responses (Alaniz et al., 2007. Romeu et al., 2013++)

*F. tularensis* ssp. has previously been shown to produce vesicles in in vitro cultured infected macrophages (Anthony et al., 1991; Golovliov et al., 2003). Recent work has shown that similar vesicles could be isolated from broth cultured *F. tularensis* ssp. *novicida* and *F. philomiragia* ssp. *philomiragia* (Pierson et al., 2011), and that these vesicles were derived by budding from the outer bacterial membrane (McCaig et al., 2013) thereby being true OMVs. Macrophages treated with the vesicles released proinflammatory cytokines, and mice vaccinated with OMVs were protected against subsequent challenge with *F. tularensis* ssp. *novicida* (Pierson et al., 2011; McCaig et al., 2013). Interestingly, in addition to regular spherical vesicles, OMVs from *F. tularensis* can also be shaped like tubes (McCaig et al., 2013). Previously, Bakkemo et al., (2011) showed by EM that also *F. noatunensis* ssp. *noatunensis* releases vesicles in vitro in infected macrophages, but as they could not detect vesicles from extracellular cultured bacteria, they hypothesized that the formation of vesicles from *F. noatunensis* ssp. *noatunensis* was an intracellular event.

Systems and methods for protecting fish against infection by infectious agents are needed.

SUMMARY OF THE INVENTION

The disclosure relates to outer membrane vesicles from microorganisms, and their use in vaccine compositions in fish. In particular the disclosure relates to outer membrane vesicles from *Francisella* and *Piscirickettsia*, and their use in vaccine compositions. In particular, the present disclosure relates to compositions and methods useful in inducing protective immunity against francisellosis or salmon rickettsial septicaemia (SRS) in fish.

Accordingly, in some embodiments, the present invention provides methods and uses of inducing immunity against francisellosis (e.g., preventing or treating francisellosis disease and/or SRS) in a fish, comprising: administering a composition comprising an outer membrane vesicle of a *Francisella* spp. or a *Piscirickettsia* spp. to a fish. The present invention is not limited to a particular species of *Francisella* or *Piscirickettsia*. Examples include, but are not limited to, *Francisella noatunensis* (e.g., including but not limited to. *Francisella noatunensis* subsp. *noatunensis; Francisella noatunensis* supsp. *orientalis; F. noatunensis* subsp. *endociliophora*; or *Candidatus F. noatunensis* subsp. *endociliophora*); *Francisella phlomiragia* subsp. *philomiragia; Francisella cantonensis; Francisella victoria*; (Schrallhammer M et al., 2011); *Francisella cantonensis*; or *Piscirickettsia* spp. (e.g., including but not limited to, *Piscirickettsia salmonis* strains LF-89; (U36941); EM-90 (U36940); NOR-92 (U36942); ATL-4-91 (U36915); IRE-99D (AY498637); SCO-95A (AY498636); SCO-02A (AY498635); IRE-98A (AY498634); IRE-91A (AY498633); WSB-98; or AL10005). The uses and methods described herein find use in preventing and treating infection and disease in a variety of fish species. Examples include, but are not limited to, Atlantic cod, *Gadus morhua*; tilapia, *Oreochromis* sp.; Atlantic salmon, *Salmo salar*; trout, *Onco-*

*rhynchus mykiss* hybrid striped bass, *Morone chrysops*×*M. saxatilis* or three-lined grunt, *Parapristipoma trilinineatum*.

Additional embodiments are described herein.

DEFINITIONS

Figure 1:
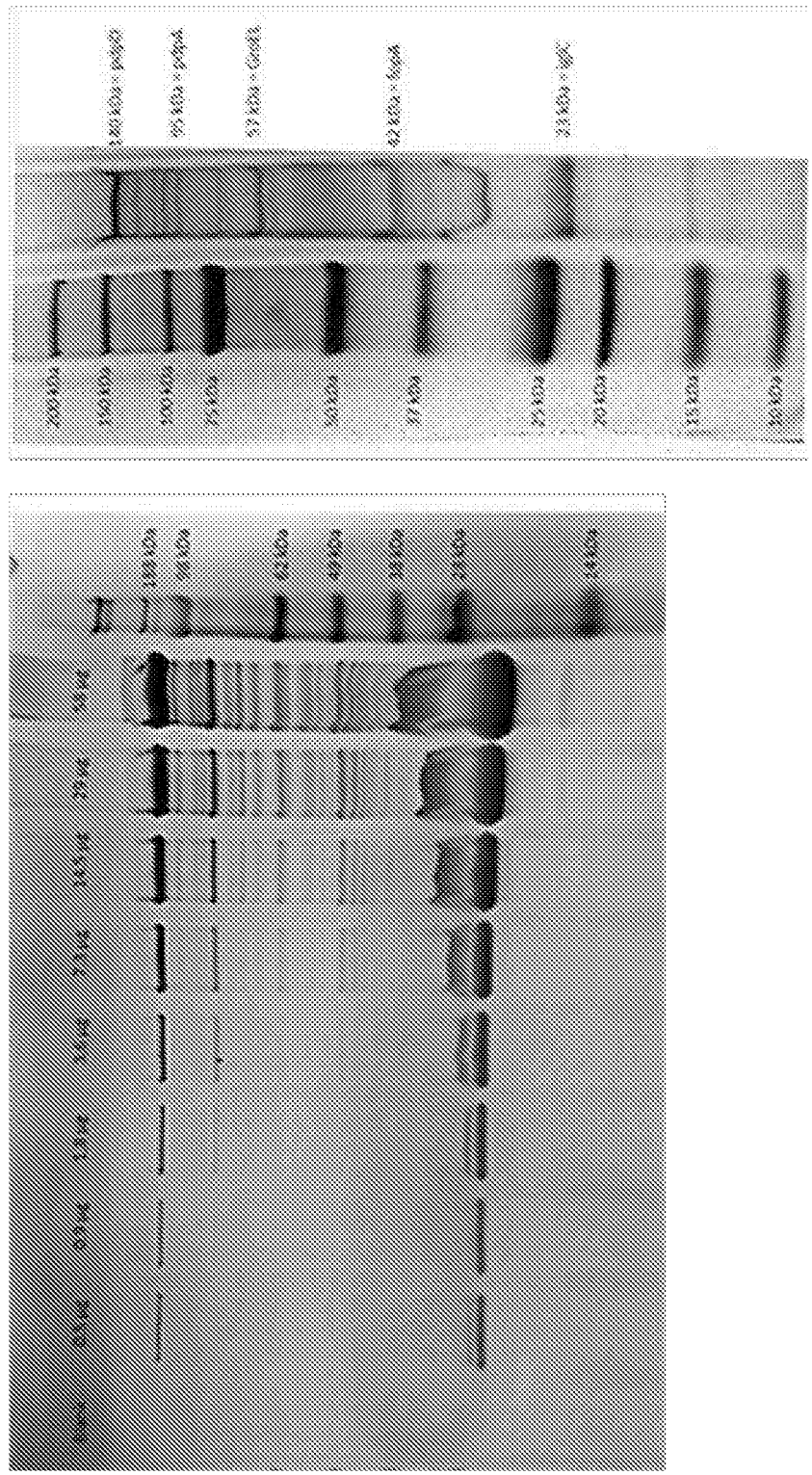
FIG. 1 shows Coomassie Blue staining of proteins from OMVs isolated from *F. noatunensis* ssp. *noatunensis*.
Figure 2:
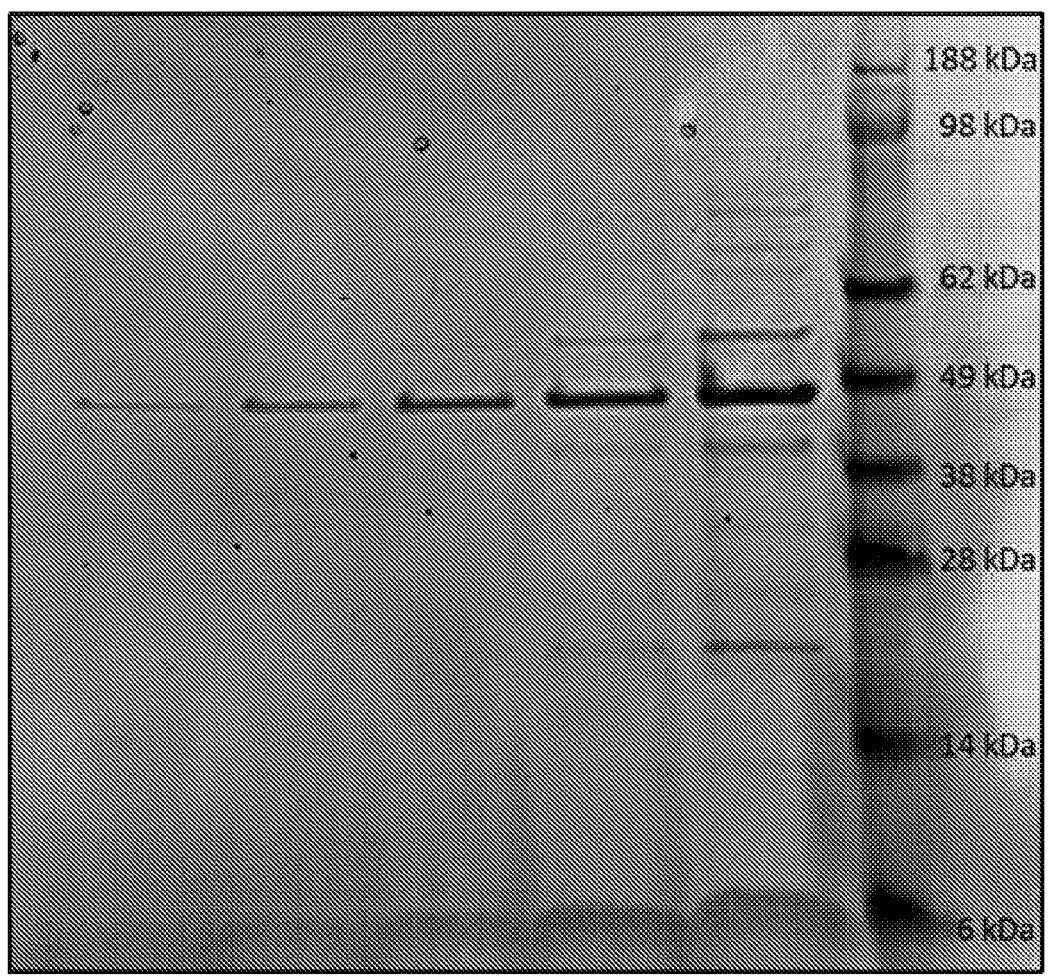
FIG. 2 shows Coomassie Blue staining of proteins from OMVs isolated from *P. salmonis*
Figure 3:
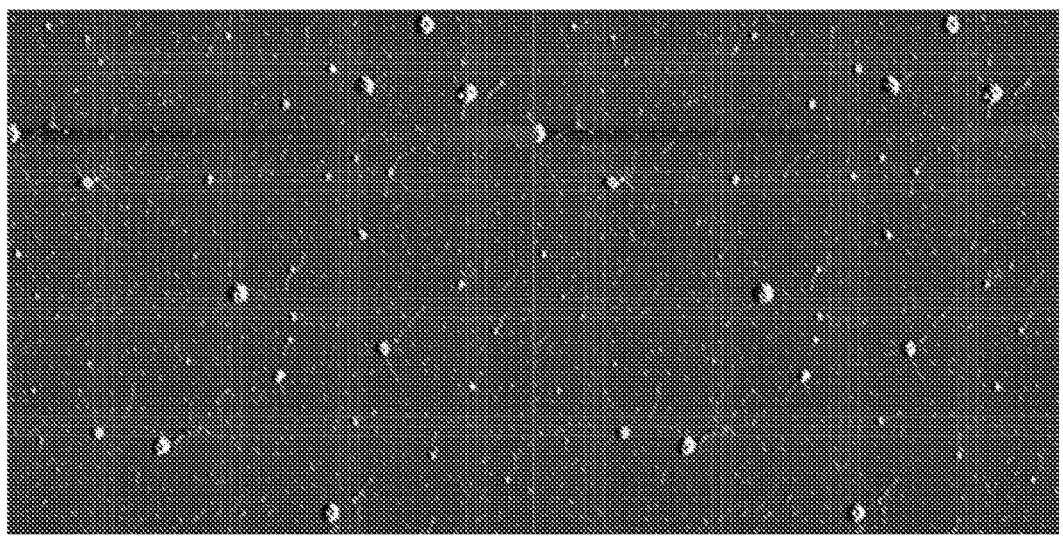
FIG. 3 shows AFM of OMV isolated from *P. salmonis*.
Figure 4:
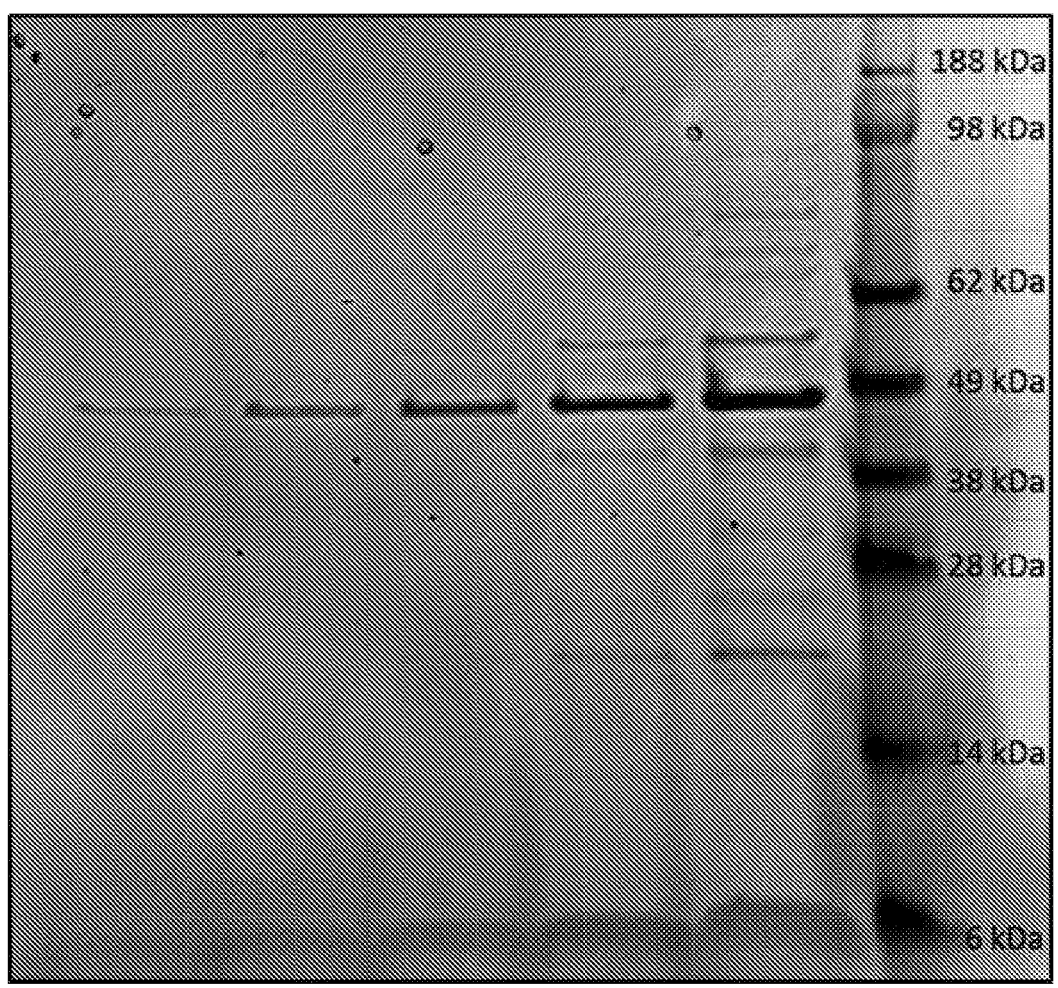
FIG. 4 shows AFM and TEM on isolated OMVs from *F. noatunensis* ssp. *noatunensis*.
Figure 5:
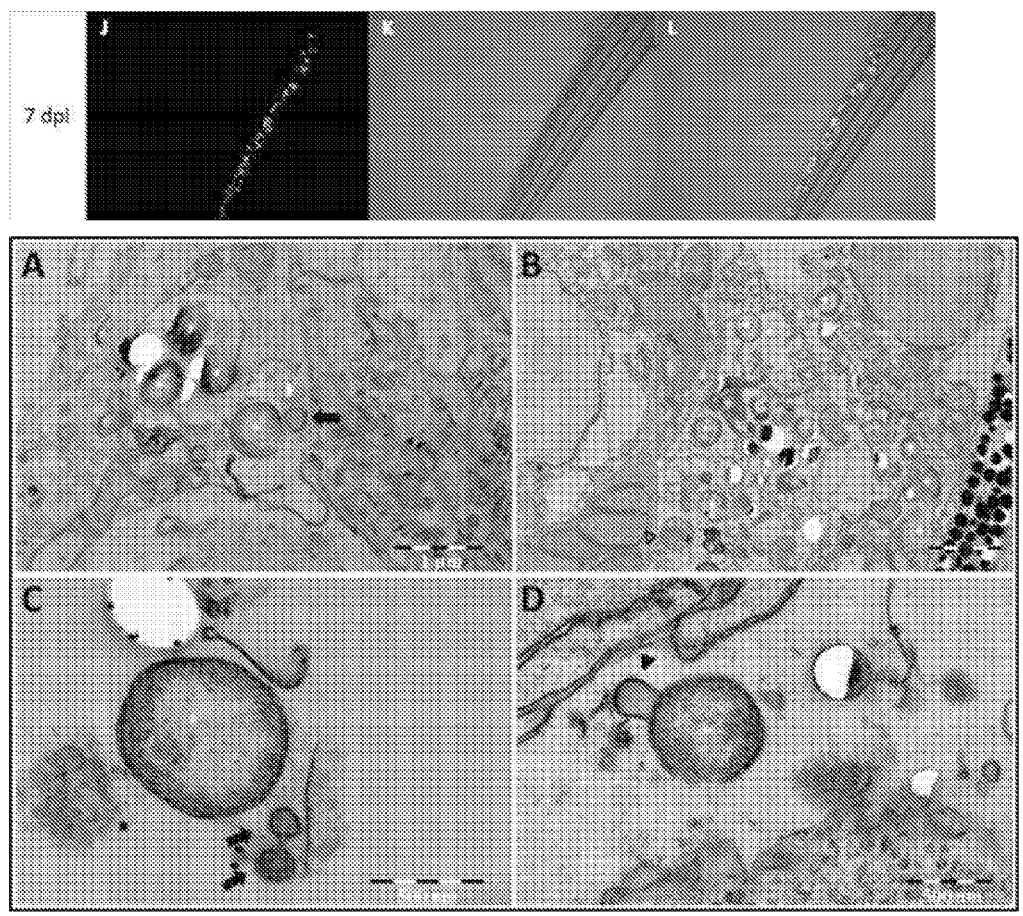
FIG. 5 shows TEM images of zebrafish embryos infected with F.n.n.-GFP revealing production of OMVs in vivo. A) TEM image of an infected zebrafish embryo revealing bacteria surrounded by OMVs in an intracellular compartment. B) TEM image of zebrafish embryo cells heavily infected with bacteria, autophagy of cellular organelles (open arrowhead) indicating apoptosis. C) TEM image of extracellular bacteria surrounded with OMVs in an infected zebrafish embryo. D) In vivo budding of OMV in the cytoplasm of an infected zebrafish embryo. Asterisks indicate F.n.n., arrows indicate OMVs, arrowhead indicate formation of OMV, open arrowhead indicate autophagic organelle.
Figure 6:
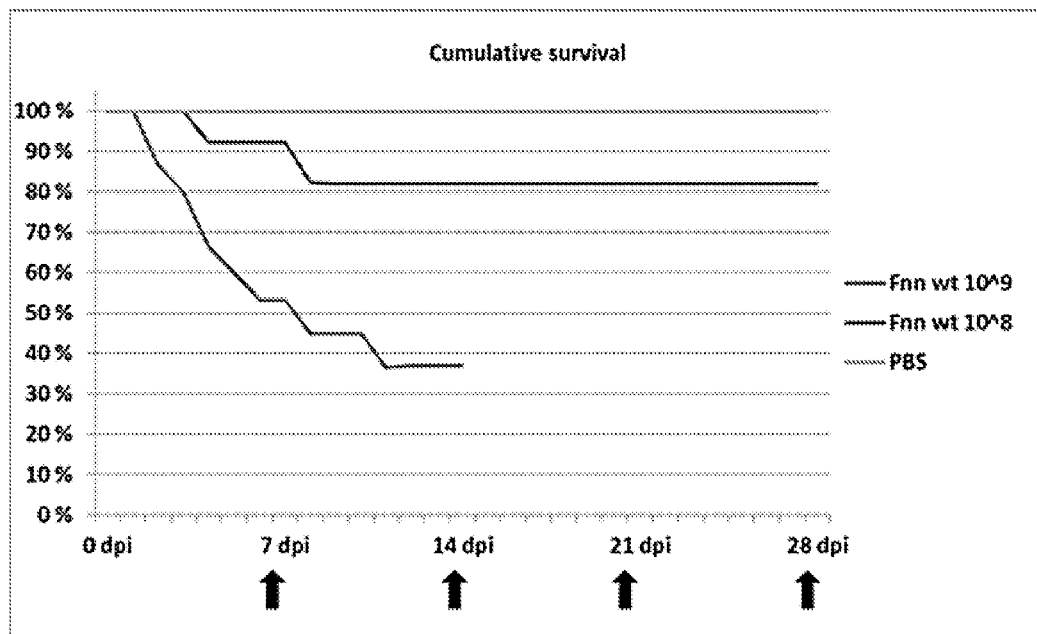
FIG. 6 shows that *F. noatunensis* ssp. *noatunensis* causes dose-dependent mortality of adult zebrafish.
Figure 7:
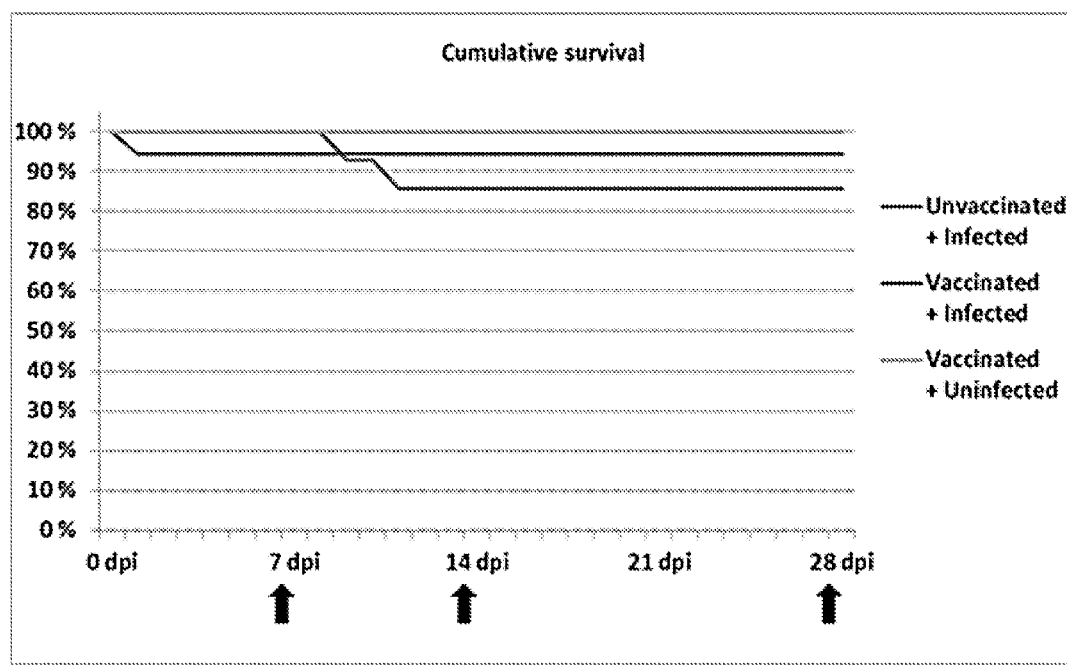
FIG. 7 shows that OMVs are safe for immunization of zebrafish and protect against subsequent challenge with *F. noatunensis* ssp. *noatunensis*.
Figure 8:
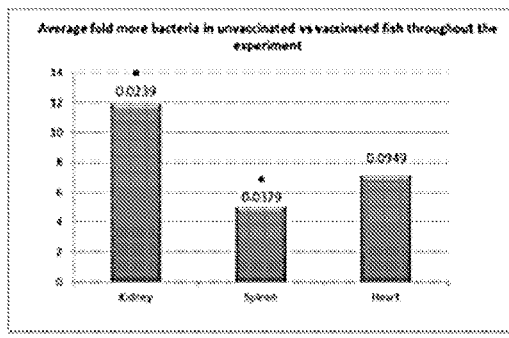
FIGS. 8 *a, b, c,* and *d* shows quantification of bacterial burden in the kidney, spleen and heart of unvaccinated and vaccinated fish.
Figure 8:
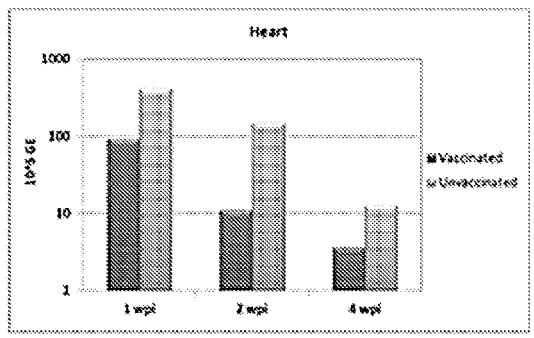
Figure 8:
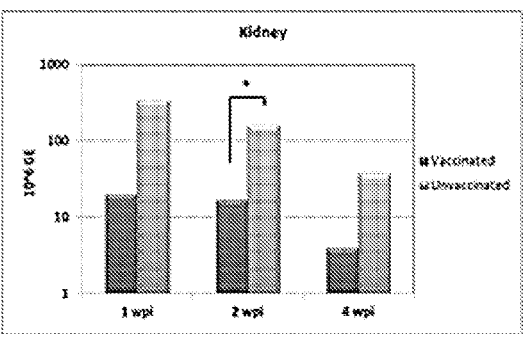
Figure 8:
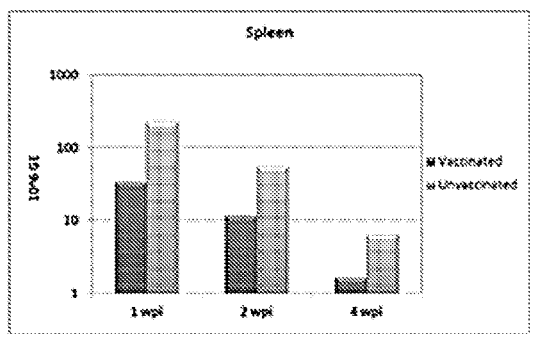
Figure 9:
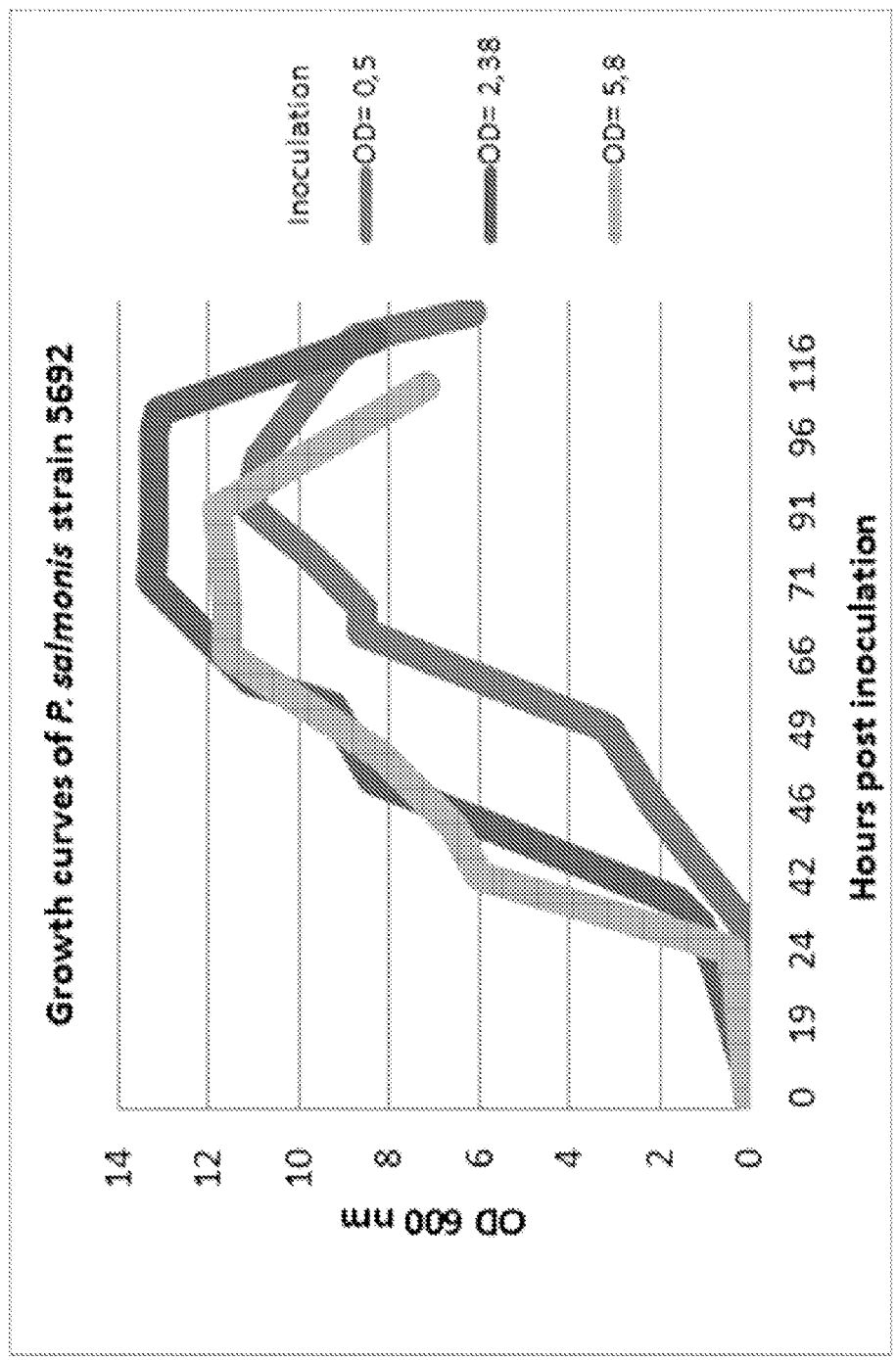
FIG. 9 shows growth curves of *P. salmonis* in Eugon broth supplemented with Casamino acids.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen)) that is capable of eliciting an immune response in a subject. In some embodiments, immunogens elicit immunity against the immunogen (e.g., microorganism (e.g., pathogen or a pathogen product)).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The disclosure relates to outer membrane vesicles from *Francisella* and *Piscirickettsia*, and their use in vaccine compositions. In particular, the present disclosure relates to compositions and methods useful in inducing protective immunity against francisellosis or salmon rickettsial septicaemia (SRS) in fish.

Vaccinating against intracellular pathogens has always been a challenge, especially without resorting to the use of live-attenuated vaccines (Titball, 2008).

Although antibodies typically have been thought to exclusively combat pathogens in the extracellular stages of infection, new information regarding the importance of antibody-mediated immunity against intracellular pathogens question this long-standing dogma (Casadevall & Pirofsky, 2006). But even though it has been proven that *Francisella* has a significant extracellular phase where bacteria would be accessible to antibodies (Forestal et al., 2007; Yu et al., 2008), and that antibodies against the LPS-O-antigen complex can award some protection against infection with *Francisella* (Sebastian et al., 2007; Cole et al., 2009), the importance of stimulating cell-mediated immunity for combating *Francisella*-infections is unquestionable. Zebrafish have been used extensively in recent years for studying host-pathogen interactions due to several reasons, such as easy housing, a fully sequenced genome and availability of genetic tools (Allen & Neely, 2010). Additionally, zebrafish have a fully functional immune system remarkably similar to mammals (Meeker & Trede 2008; Renshaw & Trede, 2012). Recently, Vojtech et al. (2009) showed that adult zebrafish were susceptible to infection with *F. noatunensis* ssp. *orientalis*. Zebrafish embryos are susceptible to *F. noatunensis* ssp. *orientalis*, and additionally to *F. noatunensis* ssp. *noatunensis* and *F. tularensis* ssp. *novicida* when the embryos were adapted to the proper temperatures for the pathogen (Brudal et al., Infect Immun. 2014 June; 82(6): 2180-94). In experiments associated with the present invention, we investigated whether adult zebrafish could be infected with *F. noatunensis* ssp. *noatuenensis*, and if zebrafish could be used to study the efficacy of OMVs as a vaccine against francisellosis. When infecting zebrafish with *F. noatunensis* ssp. *noatunensis*, a clear dose-response with regards to mortality was observed, and the onset of mortality was also earlier for the group infected with the highest dose. After an initial acute phase of infection, no more mortality could be observed, and the infection entered a chronic state. While the bacterial burden declined throughout the experiment, large amounts of bacteria were present in all examined tissues even at 4 weeks post infection.

It is contemplated that vaccination with OMVs can protect zebrafish against development of francisellosis. This was apparent from quantification of bacterial burden in tissues from infected fish, and also by a clear clinical improvement for vaccinated fish compared to unvaccinated fish.

The infectious dose was chosen due to a desire to mimic the spontaneously occurring disease as much as possible. As francisellosis in Atlantic cod is a chronic, granulomatous disease (Nylund et al., 2006; Olsen et al., 2006), we wanted to avoid an acute model of infection.

OMVs isolated from most bacteria require detergent-extraction to reduce the levels of LPS and LOS (lipo-oligosaccharides) to be safe for parenteral delivery (Collins, 2011). Detergent-extracted OMVs, as well as OMVs induced by other chemical methods such as gentamicin treatment, differ in protein content compared to native OMVs (Collins 2011; van de Waterbeemd et al., 2013). As *Francisella* spp. contains a unique LPS which is less toxic compared to most Gram negative bacteria (Gunn & Ernst, 2007), native OMVs can be isolated and used for vaccination without adverse effects. Recent studies using *F. tularensis* ssp. *novicida* OMVs used intra-nasal (i.n.) immunization with native vesicles (Pierson et al., 2011; McCaig et al., 2013). Here we show that zebrafish can be immunized with native OMVs intraperitoneally (i.p.) derived from *F. noatunensis* ssp. *noatunensis* without adverse effects.

The present invention relates to compositions, such as vaccines, and their use to elicit immune responses against *Francisella* and *Piscirickettsia* spp, especially protective immune responses in aquatic species including fish. The invention also relates to isolated outer membrane vesicles from strains of *Francisella* and *Piscirickettsia* spp which infect fish. It also relates to a method of preventing infection by *Francisella* and *Piscirickettsia* spp in fish comprising administering a vaccine of the invention, e.g., wherein said animal is a human. It further relates to a method for reducing *Francisella* and *Piscirickettsia* spp infection symptoms in fish, comprising administering to a fish or population of fish in need of such treatment an effective amount of antibodies against native outer membrane vesicles of *Francisella* in a pharmaceutically acceptable excipient or feed vehicle, or a method of eliciting an immune response against *Francisella* and/or *Piscirickettsia* spp comprising administering outer membrane vesicles from *Francisella* and/or *Piscirickettsia* spp. This invention in one aspect provides isolated or biologically pure (e.g., substantially free of toxic components) outer membrane vesicles from *Francisella* and *Piscirickettsia* spp which have been shown to infect fish as described in more detail herein. "Isolated" in general refers to the vesicles in a state other than the natural state. The invention also provides a vesicle preparation. For administration to a fish, the vesicles are preferably formulated as immunogenic compositions, and more preferably as compositions suitable for use as a vaccine in fish. Vaccines of the invention may either be prophylactic (i.e. to prevent infection) or therapeutic (i.e. to treat disease after infection), but will typically be prophylactic.

Immunogenic compositions comprise an immunologically effective amount of antigen, as well as any other compatible components, as needed. By "immunologically effective amount" is meant that the administration of that amount to an subject, such as a fish, either in a single dose or as part of a series, is effective for treatment or prevention. This amount varies depending upon the health and physical condition of the subject to be treated, age, the taxonomic group or subject to be treated (e.g., fish, etc.), the capacity of the individual's immune system to synthesize antibodies, the degree of protection desired, the formulation of the vaccine, and other relevant factors. It is expected that the amount will fall in a relatively broad range that can be determined through routine trials. Dosage treatment may be a single dose schedule or a multiple dose schedule (e.g., including booster doses). The vaccine may be administered in conjunction with other immunoregulatory agents.

Accordingly, embodiments of the present invention provide compositions and methods for immunizing fish against francisellosis. In some embodiments, the present invention provides OMV isolated from a variety of species of *Francisella*. The present invention is not limited to a particular species or strain of *Francisella*. Examples include, but are not limited to:

*Francisella noatunensis* subsp *noatunensis* (syn. *Francisella piscicida*, syn *Francisella philomiragia* subsp *noatunensis*, syn *Francisella piscicida*);

*Francisella noatunensis* supsp. *orientalis* (syn. *Francisella noatunensis* subsp *asiatica*, syn *Francisella victoria*) *Francisella philomiragia* subsp. *Philomiragia; F. noatunensis* subsp. *Endociliophora;*
- *Wolbachia persica;*
- *Francisella victoria*; (Kay W, Petersen B O, Duus JØ, Perry M B, *Vinogradov E. Characterization of the lipopolysaccharide and beta-glucan of the fish pathogen Francisella victoria. FEBS J.* 2006 July; 273(13): 3002-13. *Epub* 2006 Jun. 5.-Noda H, Munderloh U G, Kurtti T J. Endosymbionts of ticks and their relationship to *Wolbachia* spp. and tick-borne pathogens of humans and animals. Appl Environ Microbiol. 1997 October; 63(10):3926-32);
- *Candidatus F. noatunensis* subsp. *endociliophora* (Schrallhammer M et al., 2011);
- *Francisella cantonensis* Isolated from air conditioning systems (Qu P, Deng X, Zhang J, Chen J, Zhang J, Zhang Q, Xiao Y, Chen S. Identification and characterization of the *Francisella* sp. strain 08HL01032 isolated in air condition systems. Wei sheng wu xue bao Acta microbiologica sinica. 2009; 49:1003-1110); and
- *Fangia hongkongensis* (Lau K W, Ren J, Fung M C, Woo P C, Yuen K Y, Chan K K, Qian P Y, Wong P K, Wu M. *Fangia hongkongensis* gen. nov., sp. nov., a novel gammaproteobacterium of the order Thiotrichales isolated from coastal seawater of Hong Kong. *Int J Syst Evol Microbiol.* 2007 November; 57(Pt 11):2665-9).

It should be noted that there are many synonyms for these species and they have been isolated from ornamental fish to fish from marine, fresh, brackish, warm and cold water (See e.g., Colquhoun D J, Duodu S. *Francisella* infections in farmed and wild aquatic organisms. Vet Res. 2011 Mar. 8; 42(1):47. doi: 10.1186/1297-9716-42-47).

In some embodiments, the present disclosure provides OMV isolated from *Piscirickettsia salmonis*. Examples include, but are not limited to, isolates from Atlantic salmon (*Salmon salar*), coho salmon (*Oncorhynchus kisutch*) and Rainbow trout (*O. mykiss*). Other Rickettsia Like Organisms (RLOs) have been reported worldwide in different fish species (Khoo et al. 1995, Chen et al. 2000a,b). In some embodiments, the following *P. salmonis* strains are utilized:

- LF-89 (ATCC VR-1361) (-Gómez F A, Tobar J A, Henríquez V, Sola M, Altamirano C, Marshall S H. Evidence of the presence of a functional Dot/Icm type IV-B secretion system in the fish bacterial pathogen *Piscirickettsia salmonis*. PLoS One. 2013; 8(1): e54934. doi: 10.1371/journal.pone.0054934. Epub 2013 Jan. 28; Fryer J L, Lannan C N, Giovannoni S J, Wood N D. *Piscirickettsia salmonis* gen. nov., sp. nov., the causative agent of an epizootic disease in salmonid fishes. Int J Syst Bacteriol. 1992 January; 42(1):120-6);
- (U36941)
- EM-90 (U36940)
- NOR-92 (U36942)
- ATL-4-91 (U36915)
- IRE-99D (AY498637)
- SCO-95A (AY498636)
- SCO-02A (AY498635)
- IRE-98A (AY498634)
- IRE-91A (AY498633)
- WSB-98 isolate of *Piscirickettsia salmonis* originally isolated from liver tissue of moribund white seabass (Chen et al. 2000); *P. salmonis* AL10005, PHARMAQ AS, 0213 Oslo, Norway (Eliassen, T. M.; Solbakk, I. T.; Haugseth, K. T.; Bordevik, M.; Nygaard, A.; Rode, M. UK. Patent 2,452,892, 2011) or isolated described McCarthy U, Steiropoulos N A, Thompson K D, Adams A, Ellis A E, Ferguson H W (Confirmation of *Piscirickettsia salmonis* as a pathogen in European sea bass Dicentrarchus labrax and phylogenetic comparison with salmonid strains. Dis Aquat Organ. 2005 Apr. 18; 64(2):107-19).

In some embodiments, the present invention provides vaccine compositions comprising an OMV isolated from *Francisella* or *Piscirickettsia* species. In some embodiments, OMVs are administered alone or in a physiologically acceptable carrier. Physiologically acceptable carriers for vaccination of fish are known in the art and need not be further described herein. In addition to being physiologically acceptable to the fish the carrier must not interfere with the immunological response elicited by the vaccine and/or with the expression of its polypeptide product.

The vaccines of the present invention are preferably administered to fish to prevent, e.g., francisellosis or Salmon Rickettsial Septicaemia (SRS), anytime before or after hatching. The term "fish" is defined to include but not be limited to fish species including trout, salmon, carp, perch, pike, eels, and char as well as mollusks and crustaceans. The vaccine may be provided in a sterile container in unit form or in other amounts. It is preferably stored frozen, below −20.degree. C., and more preferably below −70.degree. C. It is thawed prior to use, and may be refrozen immediately thereafter.

In some embodiments, vaccine compositions comprise one or more additional agents including but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a vaccine composition comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune respone (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes. In some embodiments, adjuvants are mineral oil or Montanide ISA711.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising an immunogen of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants may be added to a composition comprising an immunogen, or, the adjuvant may be formulated with carriers, for example liposomes, or metallic salts (e.g., aluminium salts (e.g., aluminium hydroxide)) prior to combining with or co-administration with a composition.

In some embodiments, a composition comprising an immunogen comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising an immunogen of the present invention can be used therapeutically (e.g., to enhance an immune response) or as a prophylactic (e.g., for immunization (e.g., to prevent signs or symptoms of disease)). A composition comprising an immunogen of the present invention can be administered to a subject via a number of different delivery routes and methods.

For example, the compositions of the present invention can be administered to a subject (e.g., injection, orally, bath, or dip) by multiple methods, including, but not limited to, those described herein. In some embodiments, a composition comprising an immunogen of the present invention may be used to protect or treat a fish susceptible to, or suffering from, disease by means of administering a composition of the present invention via a mucosal route (e.g., an oral route). Thus, the vaccine can be administered by any suitable known method of inoculating fish including but not limited to immersion, oral administration, spraying and injection. Preferably, the vaccine is administered by mass administration techniques such as immersion as conducted by a standardized immersion protocol described by McAllister and Owens (1986), the contents of which are hereby incorporated by reference herein in its entirety. When administered by injection, the vaccines are preferably administered parenterally. Parenteral administration as used herein means administration by intravenous, subcutaneous, intramuscular, or intraperitoneal injection. Further administration may be accomplished by sonification or electroporation.

Thus, in some embodiments, a composition comprising an immunogen of the present invention may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

In some embodiments, vaccine compositions are co-administered with one or more antibiotics. For example, one or more antibiotics may be administered with, before and/or after administration of the composition. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

In some embodiments, a vaccine composition of the present invention is formulated in a concentrated dose that can be diluted prior to administration to a fish. For example, dilutions of a concentrated composition may be administered to a subject such that the subject receives any one or more of the specific dosages provided herein. In some embodiments, dilution of a concentrated composition may be made such that a fish is administered (e.g., in a single dose) a composition comprising 0.5-50% of the amount present in the concentrated composition. In some embodiments, a composition comprising an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a fish may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration.

Dosage units may be proportionately increased or decreased based on several factors including, but not limited to, the weight of the fish and the life cycle of the fish. In addition, dosage units may be increased or decreased for subsequent administrations (e.g., boost administrations).

The vaccine may be stored in a sealed vial, ampule or the like. The present vaccine can generally be administered in the form of a spray for intranasal administration, or by nose drops, inhalants, swabs on tonsils, or a capsule, liquid, suspension or elixirs for oral administration. In the case where the vaccine is in a dried form, the vaccine is preferably dissolved or suspended in sterilized distilled water before administration. Any inert carrier is preferably used, such as saline, phosphate buffered saline, or any such carrier which the vaccine has suitable solubility. The compositions of the invention can be administered to subjects in a biologically compatible form suitable for pharmaceutical administration in vivo. By "biologically compatible form suitable for administration in vivo" is meant a form of the composition to be administered in which any toxic effects are outweighed by the therapeutic effects of the membrane vesicles.

The composition may be administered in a convenient manner such as by injection (subcutaneous, intravenous, etc.), oral administration inhalation, transdermal application, or rectal administration. The pharmaceutical compositions are therefore in solid or semisolid form, for example pills, tablets, creams, gelatin capsules, capsules, suppositories, soft gelatin capsules, gels, membranes, tubelets. For parenteral and intracerebral uses, those forms for intramuscular or subcutaneous administration can be used, or forms for infusion or intravenous or intracerebral injection can be used, and can therefore be prepared as solutions of the active membrane vesicles or as powders of the vesicles to be mixed with one or more pharmaceutically acceptable excipients or diluents, suitable for the aforesaid uses and with an osmolarity which is compatible with the physiological fluids. For local use, those preparations in the form of creams or ointments for topical use, or in the form of sprays are suitable; for inhalant uses, preparations in the form of sprays, for example nose sprays, are suitable.

It is contemplated that the compositions and methods of the present invention will find use in various settings, including research, aquaculture (e.g., for food), the wild, ornamental fish, etc. For example, compositions and methods of the present invention also find use in studies of the immune system of fish. In some embodiments, the vaccine compositions find use in commercial settings (e.g., commercial fish farming). The vaccines find use in immunizing a variety of species of fish. Examples include, but are not limited to, Atlantic cod, *Gadus morhua*; tilapia, *Oreochro-* mis sp.; Atlantic salmon, *Salmo solar*; hybrid striped bass, *Morone chrysops*×*M. saxatilis* and three-lined grunt, *Parapristipoma trilinineatum*.

The present invention further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

Example 1

Materials & Methods

Strains, Media and Growth Conditions.

*F. noatunensis* ssp. *noatunensis* NCIMB14265 isolated from diseased Atlantic cod *Gadus morhua* L. in Norway (Ottem et al., 2007) and *F. philomiragia* ssp. *philomiragia* ATCC25015 was kept for long term storage at −80° C. as previously described. Cultivation of bacteria on solid media was performed on ECA plates without antibiotics at 20-22° C., and liquid cultures were performed in Eugon Broth supplemented with 2 mM $FeCl_3$ as previously described (Brudal et al., 2013).

Isolation of OMVs.

For initial experiments, 10 ml overnight cultures were used to inoculate 100 ml liquid cultures until $OD_{600}$≈0.1, and grown to late-logarithmic or early stationary growth phase. The bacteria were pelleted at 15 000 g at 4° C. for 10 minutes, and the supernatant harvested. OMV-containing supernatant was sterile filtered through 0.45 µm filters, followed by a second filtration step using 0.2 µm filters to remove any contaminating cells and cell debris. 70 ml double-filtered OMV-containing supernatant was subjected to ultracentrifugation at 125 000 g at 4° C. using a Optima LE-80K Ultracentrifuge (Beckman Instruments) for 2 hours to pellet OMVs. The supernatant was removed, the pellet resuspended in 50 mM Hepes buffer pH 6.8 and OMVs were re-pelleted by a second centrifugation at 125 000 g for 30 minutes. The supernatant was removed, and the pellet resuspended in 100 µl PBS pH 7.4. Protein concentration was measured by NanoDrop. 25 µl aliquots were stored at −80° C. for long-term storage, and one aliquot streaked on an ECA plate and incubated at 20-22° C. for at least three weeks to ensure sterility. For large-scale production of OMVs, 2×350 ml culture was used, and a total volume of 420 ml double-filtered OMV containing supernatant was used for isolation.

SDS-PAGE and GC-MS.

Aliquots of OMVs were separated by SDS-PAGE followed by staining with Coomassie Blue. The major bands of interest were cut from the gel with a clean scalpel, and stored in individual eppendorf tubes at 4° C. until further processing. For preparation for GC-MS, the gel pieces were washed with HPLC water for 15 minutes, and washed twice with 50% acetonitrile (ACN) in HPLC water for 20 minutes each time. Thereafter, the gel pieces were dehydrated in 100% ACN overnight. The supernatant was discarded, the gel pieces rehydrated in 50 mM ammonium bicarbonate in HPLC water (Abb) with 3.0 mg/ml dithiothreitol and incubated at 56° C. for one hour to reduce intermolecular disulfide bonds in proteins. Subsequently, the supernatant was discarded and the samples rehydrated with 50 mM Abb containing 10 mg/ml iodoacetamide and incubated at room temperature in the dark for 45 minutes for alkylation of proteins to prevent the construction of new disulfde-bonds. The supernatant was discarded, and the samples washed three times with 50% ACN in HPLC water and dehydrated in 100% ACN. Thereafter, the samples were trypsinated with 16 ng/µl Trypsin in 50 mM Abb at 37° C. overnight. Trypsinated peptides were isolated from the gel pieces by addition of 5% formic acid (FA) in HPLC water and the supernatant removed, followed by 2 treatments with 5% FA in 50% ACN and complete dehydration in 100% ACN. The recovered protein-containing supernants were dried using Techne Sample Concentrator. The samples were resuspended in 1% FA, and solid phase extraction was performed with a C18 filter to clean up the samples. Finally, the samples were again dehydrated using Techne Sample Concentrator, and stored at −20° C. until further analysis.

Atomic Force Imaging of OMVs.

For Atomic force imaging (AFM), $MgCl_2$ was added to a final concentration of 10 mM to an aliquot of isolated OMVs, and 10 µl of the suspension was applied to a freshly cleaved mica surface. The OMVs were allowed to adhere to the surface for 10 minutes before washing the surface 8 times with 100 µl MQ water. Excess water was removed, and the specimen carefully dried with $N_2$-gas. Images were recorded in intermittent-contact mode at room temperature using a NanoWizard Microscope (JPK Instruments AG, Berlin, Germany) with a scan frequency of 1.0 Hz using ultrasharp silicon cantilevers with silicon etched probe tips, NSC35/AlBS (MikroMasch, Madrid, Spain). AFM images were analyzed using The NanoWizard® IP Image Processing Software (JPK Instruments AG). The theoretical size of the OMVs were calculated according to Pierson et al. (2011), in short we assumed that when OMVs adhere to the mica surface they assume the shape of half a sphere, calculated the volume of that half sphere based on $V=4/3\pi abc/2$ and then use the calculated volume to determine the diameter of a perfect sphere (the correct diameter of the OMV). For calculation of nanotubes we assumed that when nanotubes adhere to mica they assume the volume of half a cylinder, calculated the volume of half a cylinder based on $V=\pi r^2 h/2$ and used the calculated volume to determine what size the nanotube would be as a perfect sphere.

Transmission Electron Microscopy.

Carbon-coated grids were pretreated with poly-L-lysine for 20 minutes and washed three times with MQ water. Thereafter, one aliquot of OMVs were allowed to adhere for 10 minutes before the grids were washed three times with PBS, two times with MQ water, stained for 1 minute with 4% uranylacatate and washed once with MQ water. The grids were analyzed with a microscope.

Preparation of Bacterial Cultures for Zebrafish Infection.

Preparation of bacterial suspensions for infection experiments and calculation of CFU was performed essentially as described previously (Brudal et al., submitted). In short, *F. noatunensis* ssp. *noatunensis* was cultured in EBF, cells collected by centrifugation, resuspended in PBS pH 7.4 and $OD_{600}$ adjusted to the desired concentration. Serial dilutions was performed and plated on ECA plates for CFU estimation.

Zebrafish Embryo Infection Trial.

Infection of zebrafish embryos were performed essentially as previously described (Brudal et al., submitted). In short, 15 Zebrafish embryo AB wt were intravascularly injected with 9×10^3 CFU of *F. noatunensis* ssp. *noatunensis* pkk289KM/GFP wt and observed for a period of 7 days.

At 7 dpi, the embryos were euthanized and fixed in 10% buffered formalin at room temperature for 24 hours to ensure proper penetration of the fixative into the tissues, and thereafter stored at 4° C. until further processing. Whole zebrafish embryos were fixed.

*F. noatunensis* ssp. *noatunensis* Dose-Response Experiment in Zebrafish.

Male and female Zebrafish *Danio rerio* L. wild type strain AB 10 months of age were obtained from the Aleström Zebrafish Lab facility at the Norwegian School for Veterinary Sciences and kept in 6 liter sized fish tanks Fish were fed daily with SDS 400 Scientific Fish Food. Fish water was made by The fish were kept at room temperature (20+−2° C.) and acclimatized for at least one week prior to injections. 50% water was changed twice daily, and the water was aerated using a (mm diameter hose). The following water parameters were monitored using commercial test kits (TetraTest kit): water hardness (KH and GH), pH, $NO_2^-$, $NO_3^{2-}$, $NH_3/NH_4^+$ and $O_2$. Three groups of 15 fish each were used for the dose-response experiment. The fish were anesthetized with Tricaine methanesulfonate (MS-222, Sigma-Aldrich) 100 mg/L, transferred to a presoaked sponge with grooves cut into it to keep the fish in place with the abdomen facing upwards and injected in the intraperitoneal cavity (i.p.) with a 30 G 0.3 mm×8 mm Micro-Fine Demi needle with syringe. After infection, the fish were immediately transferred to a recovery bath before being transferred back to the holding tanks. The first group was injected with 25 µl of *F. noatunensis* ssp. *noatunensis* $OD_{600}$ in PBS 20.0 ($10^9$ cfu), the second group was injected i.p. with 25 µl of *F. noatunensis* ssp. *noatunensis* $OD_{600}$ in PBS 2.0 ($10^8$ cfu) and the third group injected i.p. with 25 µl PBS. Mortality was recorded twice daily, and moribound fish were euthanized with 300 mg/L Tricaine methanesulfonate due to ethical considerations.

Immunization of Zebrafish with OMVs.

Three tanks with 10 month old zebrafish AB wt, 18 fish in each tank, were acclimatized for 2 weeks prior to immunization experiments. 2 groups were anesthetized as previously described and vaccinated i.p. with 40 µg OMVs in 25 µl PBS, while the third group was mock-vaccinated with 25 µl PBS. One month later (637 degree-days) one OMV vaccinated and the PBS mock-vaccinated group were injected i.p. with 25 µl *F. noatunensis* ssp. *noatunensis* $OD_{600}$ in PBS 2.0 ($10^8$ CFU), while the remaining OMV vaccinated group was mock-infected i.p. with 25 µl PBS.

Quantification of Bacterial Burden.

For the dose-response experiment, three randomly chosen fish from each group were euthanized as previously described at each time point. For the vaccination experiment, the number of fish at each time point was 4. Necropsy was performed on all euthanized fish, and the spleen, heart and kidney harvested, transferred to RNAlater (Ambion) and stored at 4° C. until further processing. RNAlater was removed, and the samples transferred to 2.0 ml SafeLock Eppendorf tubes containing 100 µl lysis buffer with 20 mg/ml lysozyme (Sigma-Aldrich) and a 0.5 mm diameter stainless steel bead (QIAGEN). The tissue was homogenized by TissueLyser II at 15 Hz for 20 seconds, and genomic DNA (gDNA) extracted with the QIAGEN DNEasy Blood & Tissue Mini kit according to the manufacturers instructions. 100 µl DEPC treated $H_2O$ was used for elution of gDNA, and 10 µl of the eluate was diluted 1:10 in DEPC $H_2O$ and used as template for qPCR.

The previously published diagnostically validated primer pair targeting a hypothetical protein in *F. noatunensis* ssp. *noatunensis* with accession number JQ780324 (Duodu et al., 2013) was chosen for absolute quantification of the amount of *F. noatunensis* ssp. *noatunensis* genome equivalents (GE) in each fish tissue. Quantitative PCR was performed in triplicates using Express SYBR GreenER qPCR Supermix Universal (Life Technologies Inc.), 50 µM Rox Reference dye, 300 µM forward and reverse primers, and 5 µl template (corresponding to ½₀₀ of the total amount of extracted gDNA for each well) and a Stratagene Mx3005p qPCR machine. The qPCR reaction conditions were as followed: 2 minutes at 50° C., 2 minutes at 95° C., followed by 40 cycles 15 seconds at 95° C. and 1 minute at 60° C. Melting curve analysis of the PCR product was performed to verify single amplification peaks. The primer binding efficiency was validated using serial 10-fold dilutions of gDNA isolated from zebrafish tissue as described by Duodu et al. (2013), and similar results were obtained as Duodu et al (2013) obtained from Atlantic cod tissue with *F. noatunensis* ssp. *noatunensis*. The calculated primer binding efficiency was used to estimate the relative amount of *F. noatunensis* ssp. *noatunensis* GE compared to 1 ng of *F. noatunensis* ssp. *noatunensis* gDNA used as equilibrator on each qPCR plate, and absolute quantification was performed under the assumption that 20 fg gDNA corresponds to 10 GE for *F. noatunensis* ssp. *noatunensis* (Duodu et al., 2013).

Statistical Analysis.

Statistical analysis of the data sets was performed using JMP 8.0.2. (SAS Institute Inc., Cary, N.C., USA). Differences in bacterial quantification between groups were deemed statistically significant if $p<0.05$ using a one-tailed Student's t-test assuming unequal variance. Kaplan-Meier survival analysis (Goel et al., 2010) was used for analyzing survival, and differences between groups were deemed statistically significant if p-value <0.05 using Wilcoxon-test and Log-rank test.

Results

*F. noatunensis* ssp. *noatunensis* Produces Large Amounts of OMVs in Liquid Culture.

From 420 ml of late-log/early stationary liquid culture of *F. noatunensis* ssp. *noatunensis*, an average of 1860 µg protein was recovered. This corresponds to 2.66 µg protein per ml culture. For *F. philomiragia* ssp. *philomiragia* the corresponding value was 0.06 µg protein per ml culture. We did not investigate what culture conditions would give the optimal OMV production for *F. philomiragia* ssp. *philomiragia*. Pierson et al. (2011) did this for *F. tularensis* ssp. *novicida* and got a 86 μg OMV protein yield from 350 ml culture under optimal conditions.

OMVs Contain Numerous Proteins, Some of which are Associated with Virulence.

OMVs isolated from *F. noatunensis* ssp. *noatunensis* contain abundant proteins easily detectable by Coomassie Blue staining. GC-MS analysis of the most abundant proteins identified three proteins associated with the *Francisella* pathogenicity island (FPI), the major outer membrane protein (FopA) and a chaperonin (GroEL). The most abundant protein is IglC, followed by PdpD and PdpA.

OMVs are Isolated Intact.

To verify that OMVs were isolated intact, and that they were in the expected size range for OMVs, we performed AFM and TEM on isolated OMVs. Numerous OMVs of spherical shape were visible by AFM, though only a few nanotubes (McCaig et al., 2013) could be observed. The mean diameter of OMVs from *F. noatunensis* ssp. *noatunensis* was 72.34 nm (SD=26.17), the median diameter was 67.32 nm, and the measured size range was 24-133 nm. This corresponds well with the expected size range for OMVs (10-300 nm in diameter), and with data published by Pierson et al. (2011) for OMVs from *F. tularensis* ssp. *novicida* (97 nm) and *F. philomiragia* ssp. *philomiragia* (76 nm). Surprisingly, thin appendages were clearly visible protruding from many of the vesicles, sometimes connecting several vesicles together in a meshwork. These did not appear to be similar to the nanotubes described by McCaig et al. (2013), as they were only 0.5-1 nm in height and approximately 25 nm in width. Observed nanotubes on AFM were measured as 800-1000 nm in length, 11-18 nm in height and a width of 100-120 nm, and would have a mean diameter of 50.7 nm as perfect spheres, supporting a hypothesis that nanotubes and OMVs could be the same biological structures, possibly observed in different stages of development. On TEM images, numerous nanotubes in addition to OMVs were observed. The difference in ratio between OMVs and nanotubes on AFM and TEM might be due to difference in the ability of nanotubes to adhere to the mica surface used for AFM sample processing.

OMVs are Produced In Vivo in Infected Zebrafish Embryos.

TEM images of zebrafish embryos infected with F.n.n.-GFP verified previous observations by fluorescence microscopy (Brudal et al.,): bacteria were present both intracellular in infected cells and in the extracellular milieu. Some host cells (macrophages) were heavily infected and were in various stages of cell death, and while we could find bacteria intracellularly in other cell types as well (such as endothelial cells) these did not appear to be dying. OMVs could be observed in the near vicinity of bacteria in infected host tissues, and in rare events OMVs could be observed budding from the bacteria.

*F. noatunensis* ssp. *noatunensis* Causes Dose-Dependent Mortality of Adult Zebrafish.

Onset of mortality for zebrafish that were infected with the highest dose ($10^9$ cfu) occurred at 2 dpi, while there was an initial delay in onset of mortality for the group infected with $10^8$ cfu, starting at 4 dpi. No mortality was observed in the PBS injected controls. All infected fish exhibited decreased appetite and decreased motility, and moribound fish had erratic swimming behavior. At 14 dpi, all remaining fish in the high infection group (n=3) were sampled for quantification of bacterial burden, and that group was therefore terminated. Mortality in the $10^8$ cfu infected group was observed on day 4 and 9, and thereafter no mortality was observed until the end of the observation period at 28 dpi. Significant difference in survival between groups infected with high and low dose was observed (p-value 0.0142 wilcoxon test, p-value 0.0142 log-rank test).

OMvs are Safe for Immunization of Zebrafish, and Protects from Subsequent Challenge with *F. noatunensis* ssp. *noatunensis*.

One fish vaccinated with OMVs developed problems with keeping afloat in the water and was euthanized. Upon necropsy, inflammation and deflation of the anterior segment of the swim bladder was evident, probably caused by puncture of this site due to an unfortunate injection. No other evidence of discomfort due to vaccination was observed, the fish were eating and behaving normally from the first day after vaccination. After infection, initially one fish died in the group vaccinated with OMVs and infected with $10^8$ cfu *F. noatunensis* ssp. *noatunensis* in the first day. This might have been due to damage from the injection, as the fish was quite pale upon necropsy. Unvaccinated+infected fish exhibited anorexia and decreased motility as in the first experiment for the first two weeks of the experiment, while the vaccinated+infected fish had slight decrease in appetite the first couple of days, but much less reduced compared to the unvaccinated group and was undistinguishable from the control group at 4 dpi. The vaccinated+uninfected group exhibited no clinical symptoms throughout the experiment.

Quantification of bacterial burden showed approximately a 11 fold higher bacterial burden in the kidney of unvaccinated compared to vaccinated fish throughout the experiment (p-value 0.0239), while the corresponding numbers for spleen and kidney was 5-fold (p-value 0.0379) and 4-fold (p-value 0.0949) respectively. The relative amount of GE between vaccinated and unvaccinated fish in each tissue type was quite stable for all tissues regardless of time point examined, while the absolute quantification of GE was at the highest level at the first time point examined (1 week) and declined during the course of infection.

Example 2. Liquid Culture Growth of *P. SALMONIS* to High Densities

Materials & Methods

Strains, media and growth conditions. *P. salmonis* was kept for long term storage at −80° C. in 10% skimmed milk or in Eugon broth supplemented with 20% glycerol. Cultivation of bacteria on solid media was performed on ECA plates, and liquid cultures were performed in Eugon Broth supplemented with 0.1% Casamino acid (BD suppliers).

OMV Isolation From *P. salmonis*.

2×10 ml overnight cultures were used to inoculate 2×100 ml liquid cultures of *P. salmonis* in Eugon broth supplemented with Casamino acids and grown overnight to mid-logarithmic growth phase. The bacteria were pelleted at 15 000 g at 4° C. for 10 minutes, and the supernatant harvested. OMV-containing supernatant was sterile filtered through 0.45 μm filters, followed by a second filtration step using 0.2 μm filters to remove any contaminating cells and cell debris. 140 ml double-filtered OMV-containing supernatant was subjected to ultracentrifugation at 125 000 g at 4° C. using a Optima LE-80K Ultracentrifuge (Beckman Instruments) for 2 hours to pellet OMVs. The supernatant was removed, the pellet resuspended in 50 mM Hepes buffer pH 6.8 and OMVs were re-pelleted by a second centrifugation at 125 000 g for 30 minutes. The supernatant was removed, and the pellet resuspended in 100 μl PBS pH 7.4. Protein concentration was measured by NanoDrop. 25 μl aliquots were stored at −80° C. for long-term storage, and one aliquot streaked on an ECA plate and incubated at 20-22° C. for at least three weeks to ensure sterility.

Initial Characterization of *P. salmonis* OMVs 2-fold dilution series of OMVs isolated from *P. salmonis* were subjected to SDS-PAGE followed by Coomassie staining to identify the major protein content. Atomic force microscopy imaging was performed to verify that *P. salmonis* OMVs were isolated intact, essentially as described for *F. noatunensis* OMVs. $MgCl_2$ was added to a final concentration of 10 mM to an aliquot of isolated OMVs, and 10 μl of the suspension was applied to a freshly cleaved mica surface. The OMVs were allowed to adhere to the surface for 10 minutes before washing the surface 8 times with 100 μl MQ water. Excess water was removed, and the specimen carefully dried with $N_2$-gas. Images were recorded in intermittent-contact mode at room temperature using a NanoWizard Microscope (JPK Instruments AG, Berlin, Germany) with a scan frequency of 1.0 Hz using ultrasharp silicon cantilevers with silicon etched probe tips, NSC35/AlBS (MikroMasch, Madrid, Spain). AFM images were analyzed using The Nano Wizard® IP Image Processing Software (JPK Instruments AG). The theoretical size of the OMVs were calculated according to Pierson et al. (2011), in short we assumed that when OMVs adhere to the mica surface they assume the shape of half a sphere, calculated the volume of that half sphere based on V=4/3πabc/2 and then use the calculated volume to determine the diameter of a perfect sphere (the correct diameter of the OMV).

Results

Eugon broth supplemented with casamino acids supported the growth of *P. salmonis* to high optical densities. OMVs isolated from mid-logarithmic cultures yielded 128.3 μg OMV proteins from 140 ml double-filtered OMV-containing supernatant, a yield of 0.92 μg pr ml culture. The dominating *P. salmonis* OMV protein as evaluated by Coomassie blue staining had an apparent molecular weight of approximately 47 kDa, but several additional distinct bands of lower and higher molecular weight were also present in the sample. AFM imaging verified that OMVs were isolated intact. The mean calculated diameter of *P. salmonis* OMVs was 47.6 nm.

Example 3. Immune Response of Adult Zebrafish Against High ($1\times10^{10}$ and Lower ($1\times10^7$) Dose of *P. Salmonis* and Against Exposure of OMV Isolated from *P. SALMONIS*

Adult zebrafish were infected with $1\times10^{10}$ or $1\times10^7$ CFU of *P. salmonis*. Fish infected with 1010 CFU started to die after 3 days, while fish infected with 107 CFU started to die after 5 days. 50% of the fish in both groups were dead after 6 days.

Adult zebrafish were then injected with 40 ug OMV isolated from *P. salmonis*. No toxicity was observed after 7 days.

Figure 10:
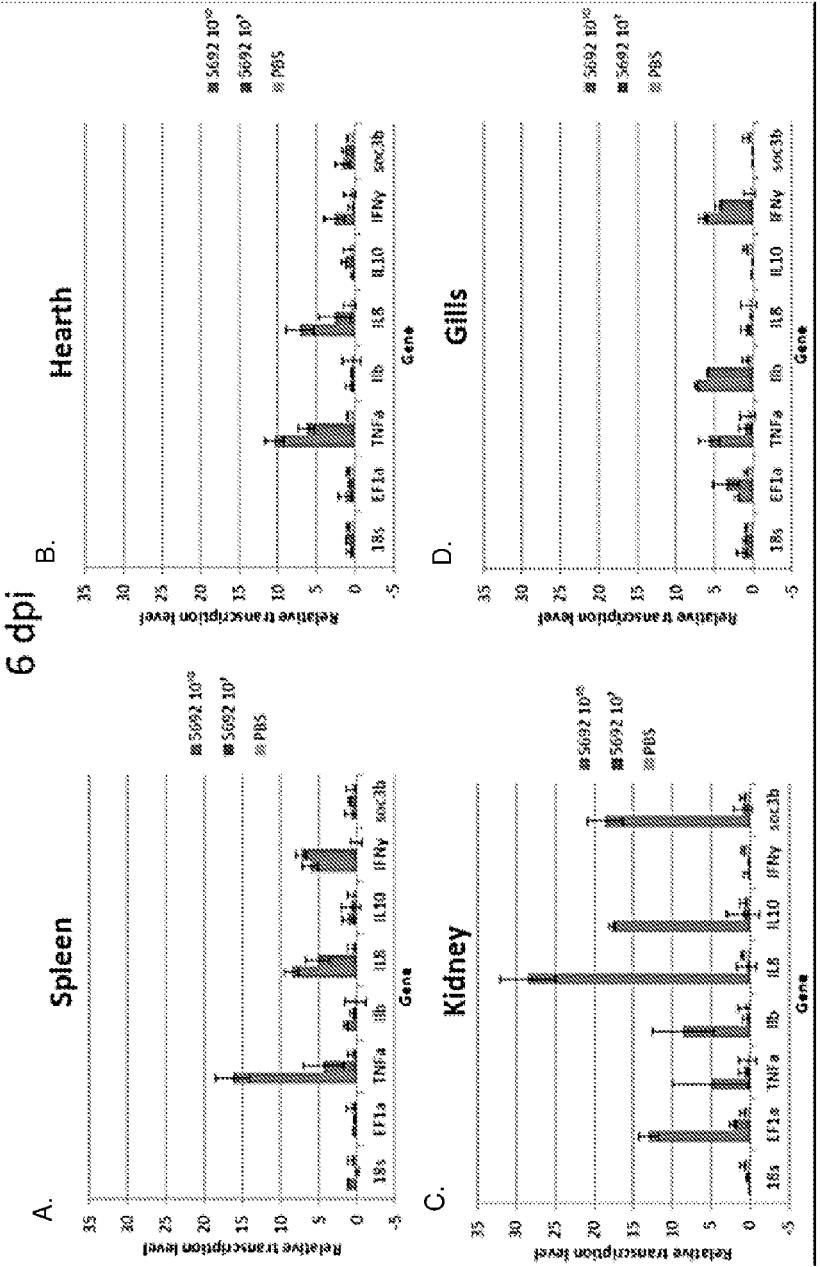
FIGS. 10 *a, b, c* and *d* provide bar graphs of levels of expression of various genes in the specified organs of zebrafish infected with *P. salmonis*.
Figure 11:
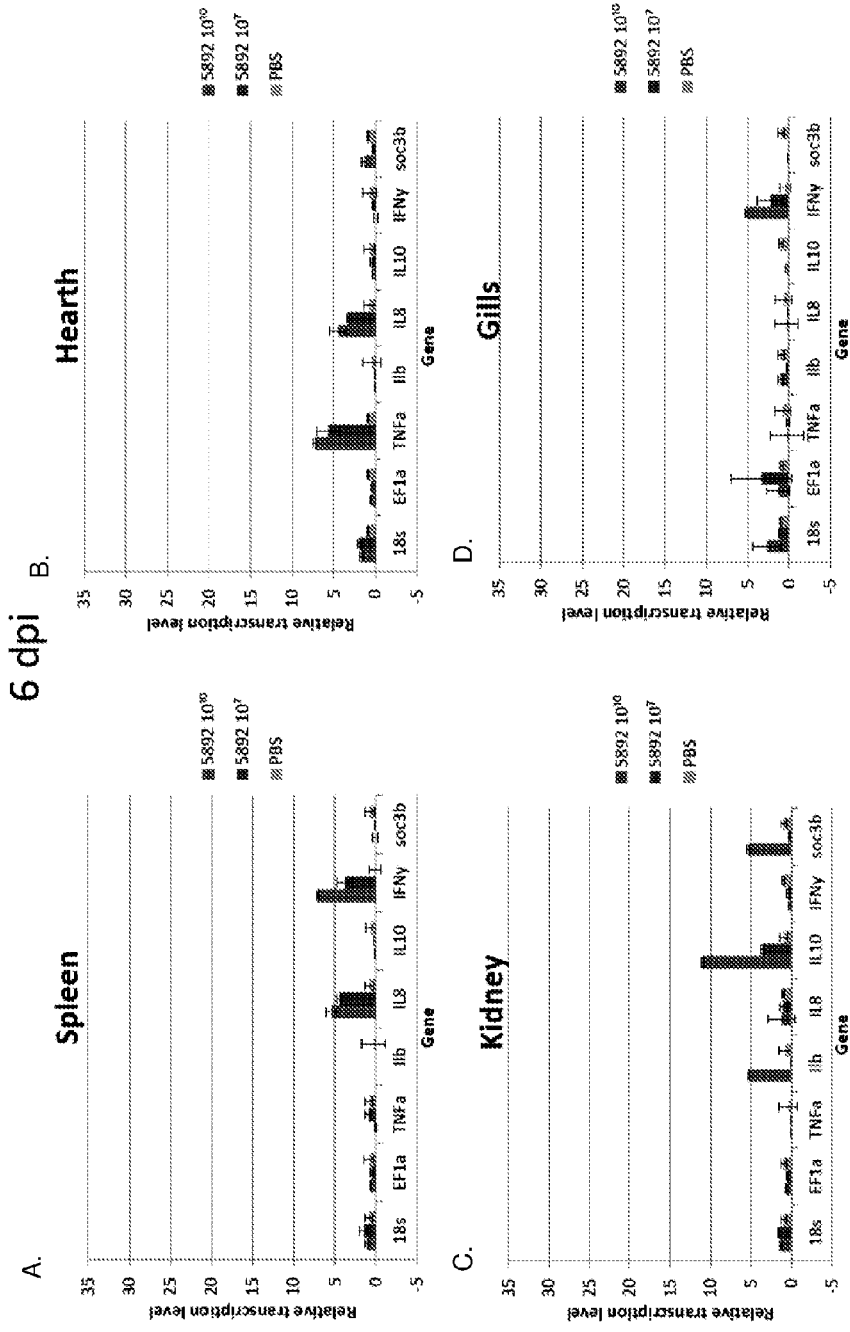
FIGS. 11 *a, b, c* and *d* provide bar graphs of levels of expression of various genes in the specified organs of zebrafish infected with *P. salmonis*.
Figure 12:
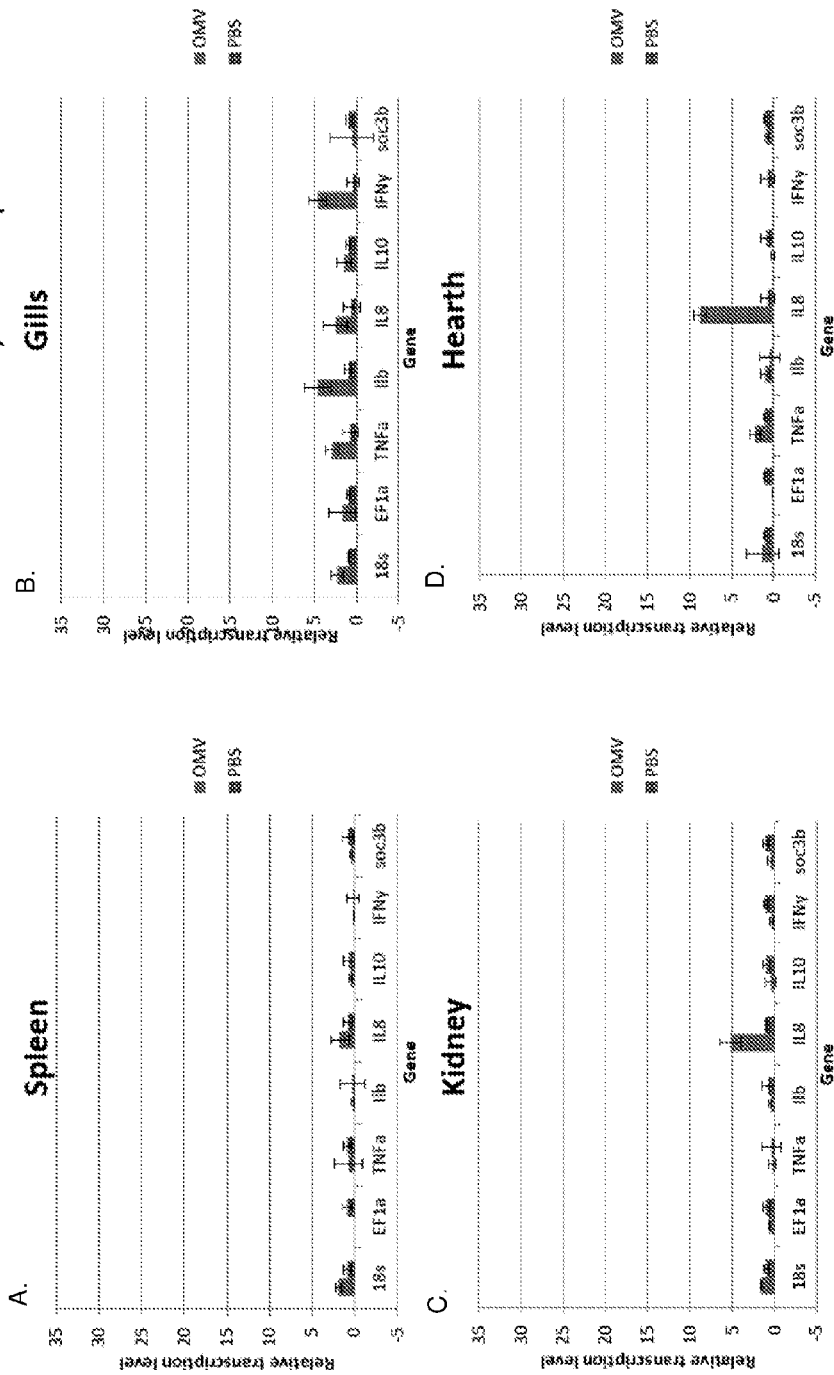
FIGS. 12 *a, b, c* and *d* provide bar graphs of levels of expression of various genes in the specified organs of zebrafish injected with OMVs isolated from *P. salmonis*.

Immune responses were analyzed in the spleen, heart, kidney and gills of zebrafish infected with *P. salmonis* (FIGS. 10 *a, b, c* and *d* and 11 *a, b, c* and *d*) and injected with OMVs isolated from *P. salmonis* (FIGS. 12 *a, b, c* and *d*). The zebrafish infected with *P. salmonis* strain 5692 induced an overall high pro-inflammatory immune response with tnfa suggesting a high initial response to the infection. Similar responses have been detected in Atlantic salmon infected with *P. salmonis* (Tacchi et al., Physiological Genomics, 2011, 43:21 1241-54). Here, the response was reduced in the $10^7$ challenge dose compared to the higher $10^{10}$ challenge dose suggesting a dose-response effect of the pathogen in the infection model. The high expression in the kidney of most immune genes tested, including il8, could be explained by the fact that the kidney is a major immune organ in fish and early immune responses are often found in this tissue. Many pathogens including *Francisella* utilize the suppression of cytokine signaling (SOCS) pathways to inhibit the host's ability to clear an infection (Brudal et al., 2014). Interestingly, the effect of zebrafish infection with *P. salmonis* does not increase in transcription of the soc3b gene, except for the very high dose $10^{10}$ in the kidney suggesting the *P. salmonis* does not suppress cytokine signaling in the same way as *Francisella* infections in the zebrafish. This is supported with the high expression of the cytokines IL8 and INFγ with the *P. salmonis* infection. Although the zebrafish immune response was reduced in the infection with the 5892 strain isolated from Atlantic salmon from Canada, the overall induction of the immune genes were similar to those detected for strain 5692. Clearly these results taken together support the zebrafish as a good infection model that inducing similar immune response as the Atlantic salmon specific for *P. salmonis* infection.

Injection with the isolated OMV form *P. salmonis* strain 5692 induced low immune responses compared to the high doses for the bacterial injections. This supports our previous results that OMV are not toxic for the host. Still, the OMV modulate an immune response that is different from the infection and the PBS control which is important for vaccine function.

REFERENCE LIST

1. Alaniz, R. C., B. L. Deatherage, J. C. Lara, and B. T. Cookson. 2007. Membrane vesicles are immunogenic facsimiles of *Salmonella typhimurium* that potently activate dendritic cells, prime B and T cell responses, and stimulate protective immunity in vivo. J. Immunol. 179: 7692-7701. doi:179/11/7692 [pii].
2. Alugupalli, K. R. 2008. A distinct role for B1b lymphocytes in T cell-independent immunity. Curr. Top. Microbiol. Immunol. 319:105-130.
3. Anthony, L. D., R. D. Burke, and F. E. Nano. 1991. Growth of *Francisella* spp. in rodent macrophages. Infect. Immun. 59:3291-3296.
4. Avila-Calderon, E. D., A. Lopez-Merino, N. Jain, H. Peralta, E. O. Lopez-Villegas, N. Sriranganathan, S. M. Boyle, S. Witonsky, and A. Contreras-Rodriguez. 2012. Characterization of outer membrane vesicles from *Brucella melitensis* and protection induced in mice. Clin. Dev. Immunol. 2012:352493. doi:10.1155/2012/352493 [doi].
5. Birkbeck, T. H., M. Bordevik, M. K. Froystad, and A. Baklien. 2007. Identification of *Francisella* sp. from Atlantic salmon, *Salmo salar* L., in Chile. J. Fish. Dis. 30:505-507.
6. Brudeseth, B. E., R. Wiulsrod, B. N. Fredriksen, K. Lindmo, K. E. Lokling, M. Bordevik, N. Steine, A. Klevan, and K. Gravningen. 2013. Status and future perspectives of vaccines for industrialised fin-fish farming. Fish. Shellfish. Immunol. doi:S1050-4648(13) 00597-4 [pii]; 10.1016/j.fsi.2013.05.029 [doi].
7. Casadevall, A. and L. A. Pirofski. 2006. A reappraisal of humoral immunity based on mechanisms of antibody-mediated protection against intracellular pathogens. Adv. Immunol. 91:1-44. doi:S0065-2776(06)91001-3 [pii]; 10.1016/S0065-2776(06)91001-3 [doi].
8. Cole, L. E., Y. Yang, K. L. Elkins, E. T. Fernandez, N. Qureshi, M. J. Shlomchik, L. A. Herzenberg, L. A. Herzenberg, and S. N. Vogel. 2009. Antigen-specific B-1a antibodies induced by *Francisella tularensis* LPS provide long-term protection against *F. tularensis* LVS challenge. Proc. Natl. Acad. Sci. U.S.A 106:4343-4348. doi: 0813411106 [pii]; 10.1073/pnas.0813411106 [doi].
9. Collins, B. S. 2011. Gram-negative outer membrane vesicles in vaccine development. Discov. Med. 12:7-15.
10. Colquhoun, D. J. and S. Duodu. 2011. *Francisella* infections in farmed and wild aquatic organisms. Vet. Res. 42:47. doi:doi: 10.1186/1297-9716-42-47.
11. Conlan, J. W. and P. C. Oyston. 2007. Vaccines against *Francisella tularensis*. Ann. N.Y. Acad. Sci. 1105:325-50. Epub@2007 Mar. 29.:325-350.
12. Conlan, J. W., H. Shen, I. Golovliov, C. Zingmark, P. C. Oyston, W. Chen, R. V. House, and A. Sjostedt. 2010. Differential ability of novel attenuated targeted deletion mutants of *Francisella tularensis* subspecies *tularensis* strain SCHU S4 to protect mice against aerosol challenge with virulent bacteria: effects of host background and route of immunization. Vaccine 28:1824-1831.
13. Cowley, S. C. and K. L. Elkins 2011. Immunity to francisella. Front Microbiol. 2:26. doi:10.3389/fmicb.2011.00026 [doi].

14. Duodu, S., P. Larsson, A. Sjodin, E. Soto, M. Forsman, and D. J. Colquhoun. 2012. Real-time PCR assays targeting unique DNA sequences of fish-pathogenic *Francisella noatunensis* subspecies *noatunensis* and *orientalis*. Dis. Aquat. Organ 101:225-234. doi:10.3354/dao02514 [doi].
15. Forestal, C. A., M. Malik, S. V. Catlett, A. G. Savitt, J. L. Benach, T. J. Sellati, and M. B. Furie. 2007. *Francisella tularensis* has a significant extracellular phase in infected mice. J. Infect. Dis. 196:134-137. doi:JID37656 [pii]; 10.1086/518611 [doi].
16. Galka, F., S. N. Wai, H. Kusch, S. Engelmann, M. Hecker, B. Schmeck, S. Hippenstiel, B. E. Uhlin, and M. Steinert. 2008. Proteomic characterization of the whole secretome of *Legionella pneumophila* and functional analysis of outer membrane vesicles. Infect. Immun. 76:1825-1836. doi:IAI.01396-07 [pii]; 10.1128/IAI.01396-07 [doi].
17. Goel, M. K., P. Khanna, and J. Kishore. 2010. Understanding survival analysis: Kaplan-Meier estimate. Int. J. Ayurveda. Res. 1:274-278. doi:10.4103/0974-7788.76794 [doi].
18. Golovliov, I., V. Baranov, Z. Krocova, H. Kovarova, and A. Sjostedt. 2003. An attenuated strain of the facultative intracellular bacterium *Francisella tularensis* can escape the phagosome of monocytic cells. Infect. Immun. 71:5940-5950.
19. Granoff, D. M. 2010. Review of meningococcal group B vaccines. Clin. Infect. Dis. 50 Suppl 2:S54-S65. doi:10.1086/648966 [doi].
20. Gunn, J. S. and R. K. Ernst. 2007. The structure and function of *Francisella* lipopolysaccharide. Ann. N.Y. Acad. Sci. 1105:202-218. doi:annals.1409.006 [pii]; 10.1196/annals.1409.006 [doi].
21. Haurat, M. F., J. Aduse-Opoku, M. Rangarajan, L. Dorobantu, M. R. Gray, M. A. Curtis, and M. F. Feldman. 2011. Selective sorting of cargo proteins into bacterial membrane vesicles. J. Biol. Chem. 286:1269-1276. doi:M110.185744 [pii]; 10.1074/jbc.M110.185744 [doi].
21b. Henriquez M, Gonzalez E, Marshall S H, Henriquez V, Gomez F A, martinez I and Altamirano C. 2013. A Novel Liquid Medium for the Efficient Growth of the Salmonid Pathogen *Piscirickettsia* salmonis and Optimization of Culture Conditions. Plos One. 8: e71830. doi:10.1371/journal.pone.0071830.
22. Jeffery, K. R., D. Stone, S. W. Feist, and D. W. Verner-Jeffreys. 2010. An outbreak of disease caused by *Francisella* sp. in Nile tilapia *Oreochromis niloticus* at a recirculation fish farm in the UK. Dis. Aquat. Organ 91:161-165.
23. Jones, R. M., M. Nicas, A. Hubbard, M. D. Sylvester, and A. Reingold. 2005. The Infectious Dose of *Francisella tularensis* (Tularemia). Applied Biosafety 10:227-239.
24. Kamaishi, T., Y. Fukuda, M. Nishiyama, M. Kawakami, T. Matsuyama, T. Yoshinaga, and N. Oseko. 2005. Identification and Pathogenicity of Intracellular *Francisella* Bacterium in Three-line Grunt *Parapristipoma trilineatum*. Fish Pathology 40:67-71.
25. Kamaishi, T., S. Miwa, E. Goto, T. Matsuyama, and N. Oseko. 2010. Mass mortality of giant abalone *Haliotis gigantea* caused by a *Francisella* sp. bacterium. Dis. Aquat. Organ 89:145-154.
26. Kuehn, M. J. and N. C. Kesty. 2005. Bacterial outer membrane vesicles and the host-pathogen interaction. Genes Dev. 19:2645-2655. doi:19/22/2645 [pii]; 10.1101/gad.1299905 [doi].
27. Lund, V., S. Bordal, O. Kjellsen, H. Mikkelsen, and M. B. Schroder. 2006. Comparison of antibody responses in Atlantic cod (*Gadus morhua* L.) to *Aeromonas salmonicida* and *Vibrio anguillarum*. Dev. Comp Immunol. 30:1145-1155. doi:S0145-305X(06)00038-3 [pii]; 10.1016/j.dci.2006.02.004 [doi].
28. Lund, V., S. Bordal, and M. B. Schroder. 2007. Specificity and durability of antibody responses in Atlantic cod (*Gadus morhua* L.) immunised with *Vibrio anguillarum* O2b. Fish. Shellfish. Immunol. 23:906-910. doi:S1050-4648(07)00089-7 [pii]; 10.1016/j.fsi.2007.04.006 [doi].
29. Mantegazza, A. R., J. G. Magalhaes, S. Amigorena, and M. S. Marks. 2013. Presentation of phagocytosed antigens by MHC class I and II. Traffic. 14:135-152. doi:10.1111/tra.12026 [doi].
29b Mauel M J and Miller D L. 2002. Piscirickettsiosis and piscirickettsiosis-like infections in fish: a review. Vet Microbiol, 87:279-289.
30. Mauel, M. J., D. L. Miller, E. Styer, D. B. Pouder, R. P. Yanong, A. E. Goodwin, and T. E. Schwedler. 2005. Occurrence of Piscirickettsiosis-like syndrome in tilapia in the continental United States. J. Vet. Diagn. Invest 17:601-605.
31. Mauel, M. J., E. Soto, J. A. Moralis, and J. Hawke. 2007. A piscirickettsiosis-like syndrome in cultured Nile tilapia in Latin America with *Francisella* spp. as the pathogenic agent. J. Aquat. Anim Health 19:27-34. doi:10.1577/H06-025.1 [doi].
32. McCaig, W. D., A. Koller, and D. G. Thanassi. 2013. Production of outer membrane vesicles and outer membrane tubes by *Francisella novicida*. J. Bacteriol. 195:1120-1132. doi:JB.02007-12 [pii]; 10.1128/JB.02007-12 [doi].
33. Nieves, W., S. Asakrah, O. Qazi, K. A. Brown, J. Kurtz, D. P. Aucoin, J. B. McLachlan, C. J. Roy, and L. A. Morici. 2011. A naturally derived outer-membrane vesicle vaccine protects against lethal pulmonary *Burkholderia pseudomallei* infection. Vaccine 29:8381-8389. doi:S0264-410X(11)01304-1 [pii]; 10.1016/j.vaccine.2011.08.058 [doi].
34. Nylund, A., K. F. Ottem, K. Watanabe, E. Karlsbakk, and B. Krossøy. 2006. *Francisella* sp. (Family Francisellaceae) causing mortality in Norwegian cod (*Gadus morhua*) farming. Arch. Microbiol. 185:383-392.
35. Olsen, A. B., J. Mikalsen, M. Rode, A. Alfjorden, E. Hoel, K. Straum-Lie, R. Haldorsen, and D. J. Colquhoun. 2006. A novel systemic granulomatous inflammatory disease in farmed Atlantic cod, *Gadus morhua* L., associated with a bacterium belonging to the genus *Francisella*. J. Fish. Dis. 29:307-311.
36. Pammit, M. A., E. K. Raulie, C. M. Lauriano, K. E. Klose, and B. P. Arulanandam. 2006. Intranasal vaccination with a defined attenuated *Francisella novicida* strain induces gamma interferon-dependent antibody-mediated protection against tularemia. Infect. Immun. 74:2063-2071. doi:74/4/2063 [pii]; 10.1128/IAI.74.4.2063-2071.2006 [doi].
37. Park, S. B., H. B. Jang, S. W. Nho, I. S. Cha, J. Hikima, M. Ohtani, T. Aoki, and T. S. Jung. 2011. Outer membrane vesicles as a candidate vaccine against edwardsiellosis. PLoS.One. 6:e17629. doi:10.1371/journal.pone.0017629 [doi].
38. Perez-Cruz, C., O. Carrion, L. Delgado, G. Martinez, C. Lopez-Iglesias, and E. Mercade. 2013. New type of outer membrane vesicle produced by the Gram-negative bacterium *Shewanella vesiculosa* M7T: implications for DNA content. Appl. Environ. Microbiol. 79:1874-1881. doi:AEM.03657-12 [pii]; 10.1128/AEM.03657-12 [doi].
39. Pierson, T., D. Matrakas, Y. U. Taylor, G. Manyam, V. N. Morozov, W. Zhou, and M. L. van Hoek. 2011. Proteomic characterization and functional analysis of outer membrane vesicles of *Francisella novicida* suggests possible role in virulence and use as a vaccine. J. Proteome. Res. 10:954-967. doi:10.1021/pr1009756 [doi].
40. Pilström, L., G. W. Warr, and S. Stromberg. 2005. Why is the antibody response of Atlantic cod so poor? The search for a genetic explanation. Fisheries Science 71:961-971. doi:10.1111/j.1444-2906.2005.01052.
41. Renshaw, S. A. and N. S. Trede. 2012. A model 450 million years in the making: zebrafish and vertebrate immunity. Dis. Model. Mech. 5:38-47. doi:5/1/38 [pii]; 10.1242/dmm.007138 [doi].
42. Romeu, B., M. Lastre, L. Garcia, B. Cedre, A. Mandariote, M. Farinas, R. Oliva, E. Rozenqvist, and O. Perez. 2013. Combined meningococcal serogroup A and W outer-membrane vesicles activate cell-mediated immunity and long-term memory responses against non-covalent capsular polysaccharide A. Immunol.Res. doi:10.1007/s12026-013-8427-6 [doi].
43. Roy, K., D. J. Hamilton, G. P. Munson, and J. M. Fleckenstein. 2011. Outer membrane vesicles induce immune responses to virulence proteins and protect against colonization by enterotoxigenic *Escherichia coli*. Clin. Vaccine Immunol. 18:1803-1808. doi:CVI.05217-11 [pii]; 10.1128/CVI.05217-11 [doi].
44. Samuelsen, O. B., A. H. Nerland, T. Jorgensen, M. B. Schroder, T. Svasand, and O. Bergh. 2006. Viral and bacterial diseases of Atlantic cod *Gadus morhua*, their prophylaxis and treatment: a review. Dis. Aquat. Organ 71:239-254. doi:10.3354/dao071239 [doi].
45. Schild, S., E. J. Nelson, and A. Camilli. 2008. Immunization with *Vibrio cholerae* outer membrane vesicles induces protective immunity in mice. Infect. Immun. 76:4554-4563. doi:IAI.00532-08 [pii]; 10.1128/IAI.00532-08 [doi].
46. Schrøder, M. B., T. Ellingsen, H. Mikkelsen, E. A. Norderhus, and V. Lund. 2009. Comparison of antibody responses in Atlantic cod (*Gadus morhua* L.) to *Vibrio anguillarum*, *Aeromonas salmonicida* and *Francisella* sp. Fish. Shellfish. Immunol. 27:112-119. doi:S1050-4648 (08)00285-4 [pii]; 10.1016/j.fsi.2008.11.016 [doi].
47. Sebastian, S., S. T. Dillon, J. G. Lynch, L. T. Blalock, E. Balon, K. T. Lee, L. E. Comstock, J. W. Conlan, E. J. Rubin, A. O. Tzianabos, and D. L. Kasper. 2007. A defined O-antigen polysaccharide mutant of *Francisella tularensis* live vaccine strain has attenuated virulence while retaining its protective capacity. Infect. Immun. 75:2591-2602. doi:IAI.01789-06 [pii]; 10.1128/IAI.01789-06 [doi].
48. Sommerset, I., B. Krossoy, E. Biering, and P. Frost. 2005. Vaccines for fish in aquaculture. Expert. Rev. Vaccines. 4:89-101. doi:ERV040113 [pii]; 10.1586/14760584.4.1.89 [doi].
49. Soto, E., D. Fernandez, and J. P. Hawke. 2009. Attenuation of the fish pathogen *Francisella* sp. by mutation of the iglC* gene. J. Aquat. Anim Health 21:140-149.
50. Soto, E., J. Wiles, P. Elzer, K. Macaluso, and J. P. Hawke. 2011. Attenuated *Francisella asiatica* iglC mutant induces protective immunity to francisellosis in tilapia. Vaccine 10:593-598.
51. Star, B., A. J. Nederbragt, S. Jentoft, U. Grimholt, M. Malmstrom, T. F. Gregers, T. B. Rounge, J. Paulsen, M. H. Solbakken, A. Sharma, O. F. Wetten, A. Lanzen, R. Winer, J. Knight, J. H. Vogel, B. Aken, O. Andersen, K. Lagesen, A. Tooming-Klunderud, R. B. Edvardsen, K. G. Tina, M. Espelund, C. Nepal, C. Previti, B. O. Karlsen, T. Moum, M. Skage, P. R. Berg, T. Gjoen, H. Kuhl, J. Thorsen, K. Malde, R. Reinhardt, L. Du, S. D. Johansen, S. Searle, S. Lien, F. Nilsen, I. Jonassen, S. W. Omholt, N. C. Stenseth, and K. S. Jakobsen. 2011. The genome sequence of Atlantic cod reveals a unique immune system. Nature 477:207-210. doi:nature10342 [pii]; 10.1038/nature10342 [doi].
52. Titball, R. W. 2008. Vaccines against intracellular bacterial pathogens. Drug Discov. Today 13:596-600.
53. Twine, S., M. Bystrom, W. Chen, M. Forsman, I. Golovliov, A. Johansson, J. Kelly, H. Lindgren, K. Svensson, C. Zingmark, W. Conlan, and A. Sjostedt. 2005. A mutant of *Francisella tularensis* strain SCHU S4 lacking the ability to express a 58-kilodalton protein is attenuated for virulence and is an effective live vaccine. Infect. Immun. 73:8345-8352. doi:73/12/8345 [pii]; 10.1128/IAI.73.12.8345-8352.2005 [doi].
54. van de Waterbeemd, B., G. P. Mommen, J. L. Pennings, M. H. Eppink, R. H. Wijffels, L. A. van der Pol, and A. P. de Jong. 2013. Quantitative Proteomics Reveals Distinct Differences in the Protein Content of Outer Membrane Vesicle Vaccines. J. Proteome. Res. doi:10.1021/pr301208g [doi].
54b. Wilhelm V, Miguel A, Burzio L O, Rosemblatt M, Engel E, Valenzuela S, Parada G, Valenzuela P D. 2006. A vaccine against the salmonid pathogen *Piscirickettsia salmonis* based on recombinant proteins. Vaccine. 24:5083-91.
54c. Yañez A J, Valenzuela K, Silva H, Retamales J, Romero A, Enriquez R, Figueroa J, Claude A, Gonzalez J, Avendaño-Herrera R, Carcamo J G. 2012. Broth mediaum for the successful culture of the fish pathogen *Piscirickettsia salmonis*. Dis Aquat Org. 97:197-205. doi:10.3354/dao02403.
55. Yu, J. J., E. K. Raulie, A. K. Murthy, M. N. Guentzel, K. E. Klose, and B. P. Arulanandam. 2008. The presence of infectious extracellular *Francisella tularensis* subsp. *novicida* in murine plasma after pulmonary challenge. Eur. J. Clin. Microbiol. Infect. Dis. 27:323-325. doi: 10.1007/s10096-007-0434-x [doi].

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A vaccine for providing immunity in a fish against microorganisms comprising:
   a protective amount of a purified preparation of outer membrane vesicles of a microorganism and a physiologically acceptable carrier for a fish, wherein the microorganism is *Piscirickettsia* ssp.

2. The vaccine of claim 1, wherein said *Piscirickettsia* spp. is selected from the group consisting of *Piscirickettsia salmonis* strains LF-89; (U36941); EM-90 (U36940); NOR-92 (U36942); ATL-4-91 (U36915); IRE-99D (AY498637);

SCO-95A (AY498636); SCO-02A (AY498635); IRE-98A (AY498634); IRE-91A (AY498633); WSB-98; and AL10005.

3. The vaccine of claim 1, wherein said fish is selected from the group consisting of Atlantic cod, *Gadus morhua*; tilapia, *Oreochromis* sp.; Atlantic salmon, *Salmo salar*; hybrid striped bass, *Morone chrysops×M. saxatilis* and three-lined grunt, *Parapristipoma trilinineatum.*

4. The vaccine of claim 1, wherein said vaccine protects said fish against Salmon Rickettsial Septicaemia (SRS).

* * * * *